(12) United States Patent
Nakamura et al.

(10) Patent No.: US 12,067,713 B2
(45) Date of Patent: Aug. 20, 2024

(54) DETERMINATION METHOD

(71) Applicant: FUJIFILM Corporation, Tokyo (JP)

(72) Inventors: Sohichiro Nakamura, Ashigarakami-gun (JP); Ryusuke Osaki, Ashigarakami-gun (JP); Sho Onozawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 852 days.

(21) Appl. No.: 17/181,651

(22) Filed: Feb. 22, 2021

(65) Prior Publication Data
US 2021/0174506 A1    Jun. 10, 2021

Related U.S. Application Data

(63) Continuation of application No. PCT/JP2019/031687, filed on Aug. 9, 2019.

(30) Foreign Application Priority Data

Sep. 28, 2018  (JP) ................. 2018-185582

(51) Int. Cl.
*G06T 7/10* (2017.01)
*C12N 5/071* (2010.01)
*G06T 7/00* (2017.01)

(52) U.S. Cl.
CPC .......... *G06T 7/0012* (2013.01); *C12N 5/0608* (2013.01); *C12N 2506/02* (2013.01); *C12N 2506/45* (2013.01); *G06T 2207/30024* (2013.01)

(58) Field of Classification Search
None
See application file for complete search history.

(56) References Cited

U.S. PATENT DOCUMENTS

| 7,880,891 B1* | 2/2011 | Kim ................. G03H 1/0443 356/457 |
| 2004/0114800 A1 | 6/2004 | Ponomarev et al. |
| 2007/0159627 A1 | 7/2007 | Johnson |
| 2010/0060897 A1 | 3/2010 | Gustafsson |

(Continued)

FOREIGN PATENT DOCUMENTS

| JP | 2006-522805 A | 10/2006 |
| JP | 2009-521218 A | 6/2009 |

(Continued)

OTHER PUBLICATIONS

Extended European Search Report for corresponding European Application No. 19865727.2, dated Oct. 27, 2021.

(Continued)

*Primary Examiner* — Gabriel I Garcia
(74) *Attorney, Agent, or Firm* — Birch, Stewart, Kolasch & Birch, LLP

(57) ABSTRACT

A determination method of non-destructively and easily determining a state of an aggregate of a plurality of cells formed by three-dimensional culture is provided. A determination method according to the disclosed technology includes generating a phase difference image of an aggregate of a plurality of cells from a hologram obtained by imaging the aggregate, deriving a phase difference amount density by dividing a total phase difference amount that is a value obtained by integrating a phase difference amount of each of a plurality of pixels constituting the phase difference image by a volume of the aggregate, and determining a state of the aggregate on the basis of a time transition of the phase difference amount density.

17 Claims, 17 Drawing Sheets

(56) References Cited

U.S. PATENT DOCUMENTS

| | | | |
|---|---|---|---|
| 2012/0315620 A1 | 12/2012 | Watakabe et al. | |
| 2013/0202151 A1* | 8/2013 | Dauwels | G03H 1/0866 |
| | | | 382/100 |
| 2014/0073002 A1 | 3/2014 | Yamauchi et al. | |
| 2014/0113323 A1 | 4/2014 | Egelberg et al. | |
| 2015/0124259 A1* | 5/2015 | An | G01B 9/02091 |
| | | | 356/456 |
| 2018/0087021 A1 | 3/2018 | Blanchard | |
| 2020/0342599 A1 | 10/2020 | Nakamura et al. | |
| 2021/0110536 A1* | 4/2021 | Akazawa | G06T 7/136 |

FOREIGN PATENT DOCUMENTS

| | | |
|---|---|---|
| JP | 2013-236564 A | 11/2013 |
| JP | 2016-28607 A | 3/2016 |
| WO | WO 2004/079007 A2 | 9/2004 |
| WO | WO 2008/134649 A1 | 11/2008 |
| WO | WO 2014/041935 A1 | 3/2014 |
| WO | WO 2019/176427 A1 | 9/2019 |

OTHER PUBLICATIONS

Kawase et al., "Non-invasive, quantitative assessment of the morphology of [gamma]-irradiated human mesenchymal stem cells and periosteal cells using digital holographic microscopy," International Journal of Radiation Biology, vol. 92, No. 12, 2016, pp. 796-805, 13 pages total.

European Communication pursuant to Article 94(3) EPC for corresponding European Application No. 19865727.2, dated Aug. 28, 2023.

Boudejltia et al., " Quantitative analysis of platelets aggregates in 3D by digital holographic microscopy," Biomedical Optics Express, vol. 6, No. 9. Sep. 1, 2015 (published Aug. 25, 2015), pp. 3556-3563.

Carl et al., "Parameter-optimized digital holographic microscope for high-resolution living-cell analysis," Applied Optics, vol. 43, No. 36, Dec. 20, 2004, pp. 6536-6544.

Cuche et al., "Quantitative phase contrast microscopy of living cells by numerical reconstruction of digital holograms," Proc. SPIE, vol. 3604, Jan. 1999, pp. 84-89.

International Preliminary Report on Patentability and Written Opinion of the International Searching Authority (Forms PCT/IB/326, PCT/IB/373 and PCT/ISA/237) for corresponding International Application No. PCT/JP2019/031687, dated April 8. 2021, with English translation.

International Search Report (Form PCT/ISA/210) for corresponding International Application No. PCT/JP2019/031687, dated Oct. 29, 2019, with English translation.

* cited by examiner

DETERMINATION METHOD

CROSS-REFERENCE TO RELATED APPLICATIONS

This application is a Continuation of PCT International Application No. PCT/JP2019/031687 filed on Aug. 9, 2019, which claims priority under 35 U.S.C § 119(a) to Japanese Patent Application No. 2018-185582 filed on Sep. 28, 2018. Each of the above application(s) is hereby expressly incorporated by reference, in its entirety, into the present application.

BACKGROUND OF THE INVENTION

1. Field of the Invention

The disclosed technology relates to a determination method for determining a state of an aggregate of a plurality of cells.

2. Description of the Related Art

As a technology for evaluating or determining a state of a cell, for example, the following technology is known. WO2014/041935A discloses a method for discriminating a degree of differentiation of a pluripotent stem cell using a flatness of a surface of one cell or a flatness of a surface of a cell population as an index of a degree of differentiation.

JP2016-028607A discloses a method for discriminating between a differentiated colony containing differentiated pluripotent stem cells and an undifferentiated colony containing only undifferentiated pluripotent stem cells and a multilayered colony containing multilayered pluripotent stem cells on the basis of brightness in a captured image. In this method, a colony having a brightness region brighter than the first threshold value of brightness is determined to be a differentiated colony. In addition, a colony having a brightness region equal to or darker than the first threshold value is determined to be an undifferentiated colony. In addition, a colony having a brightness region equal to or darker than the first threshold value and equal to or brighter than the second threshold value is determined as an undifferentiated colony. Further, a colony having a brightness region darker than the second threshold value is determined to be a multilayered colony.

JP2013-236564A discloses a cell evaluation method characterized by comprising an image input step of inputting a captured image obtained by imaging a cell in a neural differentiation process, a neurite extraction step of extracting a neurite appearing in the cell in the neural differentiation process from an original image based on the captured image, and a neurite correspondence determination step of determining a state of the extracted neurite.

JP2006-522605A discloses a method for presenting a cellular state, the method including a step of obtaining a temporal profile of a cell by monitoring over time a genetic state related to at least one gene selected from gene derived from the cell, and a step of presenting the temporal profile.

SUMMARY OF THE INVENTION

As a culture method capable of mass production of cells, a three-dimensional culture method is known in which a sphere that is an aggregate of cells are cultured in a suspended state in a medium. In the production process of cells by the three-dimensional culture, a technology for non-destructively and simply evaluating the quality of cells in the state of spheres is required from the viewpoint of easy process control. However, at the present time, a method for evaluating spheres having various sizes randomly present in a three-dimensional space has not been established, and in particular, it is difficult to directly observe a density and survival situation of cells inside the sphere. For this reason, as disclosed in WO2014/041935A, JP2016-028607A, and JP2013-236564A, evaluation is performed by applying a conventional two-dimensional culture method, but as the number of cells to be cultured increases, the number of evaluation steps increases, and thus much manpower and much time are required. In the evaluation to which the conventional two-dimensional culture method is applied, a treatment involving cell destruction such as decomposing the sphere into a single cell or adding a fluorescent coloring agent as disclosed in JP2006-522605A is required.

An object of the disclosed technology is to non-destructively and easily determine a state of an aggregate of a plurality of cells formed by three-dimensional culture.

A determination method according to the disclosed technology includes generating a phase difference image of an aggregate of a plurality of cells from a hologram obtained by imaging the aggregate, deriving a phase difference amount density by dividing a total phase difference amount that is a value obtained by integrating a phase difference amount of each of a plurality of pixels constituting the phase difference image by a volume of the aggregate, and determining a state of the aggregate on the basis of a time transition of the phase difference amount density. According to the determination method of a disclosed technology, the state of the aggregate of a plurality of cells formed by three-dimensional culture can be determined non-destructively and easily.

In a case where the cells constituting the aggregate are the stem cells, the determination method according to the disclosed technology may include a first process of differentiating stem cells into germ layers, and determining a state of differentiation of the aggregate to the germ layers on the basis of the time transition of the phase difference amount density after executing the first process. This makes it possible to non-destructively and easily determine the state of differentiation of the aggregate to the germ layers.

The determination method according to the disclosed technology includes determining a ratio of the cells differentiated into the germ layers among the stem cells on the basis of a degree of change in the phase difference amount density after executing the first process from the phase difference amount density before executing the first process. This makes it possible to non-destructively and easily determine a ratio of cells differentiated into germ layers.

The determination method according to the disclosed technology may include a second process of further differentiating the cells, which has been differentiated into the germ layers, into specific cells after executing the first process, and determining a state of differentiation into the specific cells on the basis of the time transition of the phase difference amount density after executing the second process. This makes it possible to non-destructively and easily determine the state of differentiation to the specific cell.

The determination method according to the disclosed technology may include determining a ratio of the cells differentiated into the specific cells on the basis of a degree of change in the phase difference amount density after executing the second process from the phase difference amount density before executing the second process. This makes it possible to non-destructively and easily determine a ratio of cells differentiated into the specific cell.

In a case where the cells constituting the aggregate are the stem cells, the determination method according to the disclosed technology may include a first process of differentiating stem cells into germ layers, a second process of further differentiating the cells, which has been differentiated into the germ layers, into specific cells after executing the first process, and performing a determination for a lot to be determined including a plurality of the aggregates on the basis of the time transition of the phase difference amount density from the execution of the first process to a lapse of a predetermined period after executing the second process. This makes it possible to non-destructively and easily determine the lot to be determined.

The determination method according to the disclosed technology may include performing a determination for the lot to be determined, on the basis of a degree of deviation from reference data of the time transition of the phase difference amount density, from the execution of the first process to the lapse of the predetermined period after executing of the second process, acquired for the lot to be determined. This makes it possible to non-destructively and easily determine the lot to be determined.

The determination method according to the disclosed technology may include deriving a correction value for each of the phase difference amount densities of a plurality of the aggregates included in the lot to be determined so as to suppress a dependency of the phase difference amount density of a plurality of the aggregates included in the lot to be determined on a particle diameter of the aggregate, and performing a determination for the lot to be determined on the basis of a time transition of the correction value. This makes it possible to more accurately determine the lot to be determined.

The determination method according to the disclosed technology may include deriving a value, as a correction coefficient, obtained by dividing a frequency in each class of a frequency distribution of particle diameters of a plurality of the aggregates included in an evaluation standard lot by a frequency in a corresponding class of a frequency distribution of the particle diameters of a plurality of the aggregates included in the lot to be determined, deriving a correction value of the phase difference amount density of a plurality of the aggregates included in the lot to be determined by multiplying the phase difference amount density acquired for each of a plurality of the aggregates included in the lot to be determined by a corresponding correction coefficient, and performing a determination for the lot to be determined on the basis of a time transition of an average value of the correction values. This makes it possible to more accurately determine the lot to be determined.

The determination method according to the disclosed technology may include deriving an index value indicating a correlation between the phase difference amount density and a particle diameter of the aggregate for a plurality of the aggregates included in the lot to be determined, and performing a determination for the lot to be determined on the basis of a time transition of the index value. This makes it possible to more accurately determine the lot to be determined.

According to the disclosed technology, the state of the aggregate of a plurality of cells formed by three-dimensional culture can be determined non-destructively and easily.

DESCRIPTION OF THE PREFERRED EMBODIMENTS

Figure 1:
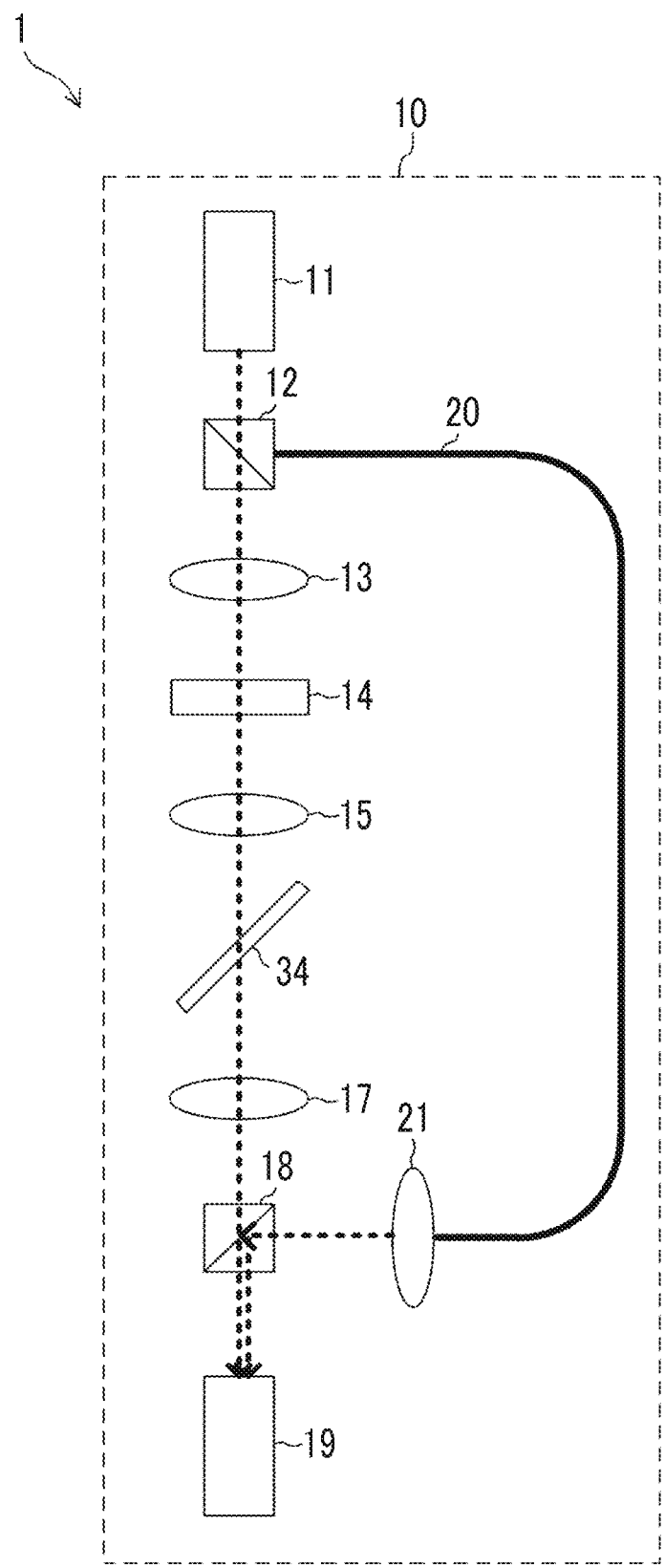
FIG. 1 is a diagram showing an example of a configuration of an imaging system used for performing a determination method according to an embodiment of the disclosed technology.

Hereinafter, embodiments of the present invention will be described with reference to the drawings. In the drawings, substantially the same or equivalent components or portions are denoted by the same reference numerals.

A determination method according to the embodiment of the disclosed technology includes generating a phase difference image of a sphere, which is an aggregate of a plurality of cells, from a hologram obtained by imaging the sphere, deriving a phase difference amount density by dividing a total phase difference amount that is a value obtained by integrating a phase difference amount of each of a plurality of pixels constituting the phase difference image by a volume of the sphere, and determining a state of the sphere on the basis of a time transition of the phase difference amount density. According to this determination method, as will be described later, it is possible to determine the state of the sphere non-destructively and simply.

FIG. 1 is a diagram showing an example of a configuration of an imaging system 1 used for performing a determination method according to an embodiment of the disclosed technology. The imaging system 1 is configured to include a hologram optical system 10 for acquiring the hologram of the sphere using a known digital holography technique.

The digital holography technique is a technique in which an image generated by interference between object light transmitted through or reflected by an object and reference light coherent with the object light is imaged using an image sensor, and numerical calculation based on light propagation is performed on the image obtained by the imaging, thereby restoring a wavefront of a light wave from the object. According to the digital holography technique, it is possible to quantify a phase distribution of the object and acquire three-dimensional information of the object without mechanically moving a focal position.

The hologram optical system 10 is configured to include a laser light source 11, beam splitters 12 and 18, collimating lenses 13 and 21, an objective lens 15, dichroic mirror 34, an imaging lens 17, and a complementary metal oxide semiconductor (CMOS) camera 19. A sphere as a sample 14 set on a sample stage is disposed between the collimating lens 13 and the objective lens 15.

As the laser light source 11, for example, a HeNe laser having a wavelength of 632.8 nm can be used. Laser light emitted from the laser light source 11 is split into two laser lights by the beam splitter 12. One of the two laser lights is object light and the other is reference light. The object light is collimated by the collimating lens 13, and then irradiated onto a sphere as the sample 14 set on the sample stage. An image formed by the object light transmitted through the sphere is magnified by the objective lens 15. The object light transmitted through the objective lens 15 is transmitted through the dichroic mirror 34, is collimated again by the imaging lens 17, and then is formed on an imaging surface of a CMOS camera 19 via the beam splitter 18. On the other hand, the reference light is guided to the front of the collimating lens 21 by the optical fiber 20. The reference light emitted from the optical fiber 20 is collimated by the collimating lens 21 and is incident on the imaging surface of the CMOS camera 19 via the beam splitter 18. The hologram generated by the interference between the object light and the reference light is recorded by the CMOS camera 19. An off-axial optical system in which optical axis directions of the object light and the reference light incident on the imaging surface of the CMOS camera 19 are different from each other may be configured.

According to the imaging system 1 according to the present embodiment, it is possible to acquire a phase difference image of the sphere without destroying the sphere and without damaging the cells constituting the sphere. The configuration of the above-described imaging system 1 is merely an example, and the present invention is not limited to the above-described configuration. Any imaging system capable of acquiring a hologram using digital holography technology can be used to perform the determination method according to the disclosed technology.

Hereinafter, an example of a method of acquiring a phase difference image of a sphere from a hologram of the sphere acquired by using the imaging system 1 will be described.

Figure 2A:
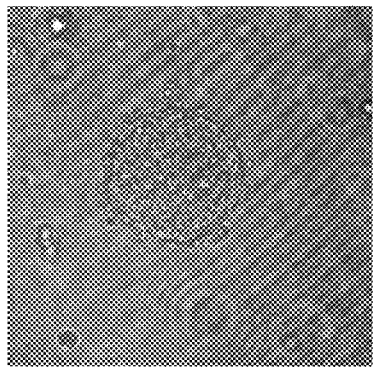
FIG. 2A is a diagram showing an example of a hologram used for performing a determination method according to an embodiment of the disclosed technology.
Figure 2B:
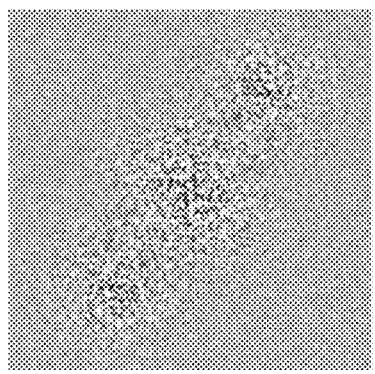
FIG. 2B is a diagram showing an example of a Fourier transform image of a sphere.

First, the hologram exemplified in FIG. 2A acquired by the CMOS camera 19 is subjected to a two-dimensional Fourier transform to extract a complex amplitude component of only the object light. FIG. 2B is an example of a Fourier transform image of the sphere obtained by this processing.

Figure 2C:
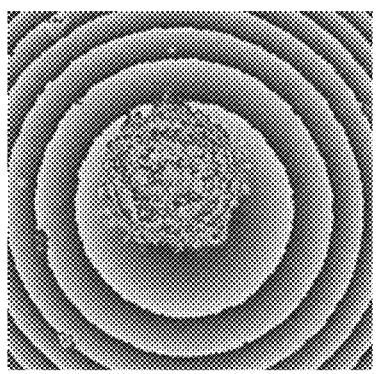
FIG. 2C is a diagram showing an example of a phase difference image of a sphere before unwrapping.
Figure 2D:
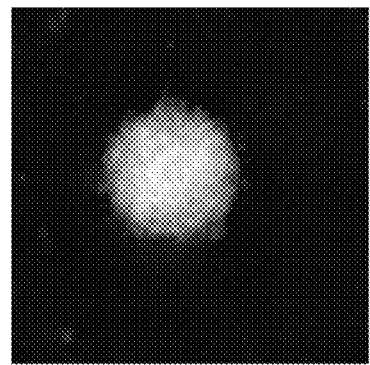
FIG. 2D is a diagram showing an example of a phase difference image of a sphere after unwrapping.

Next, for example, the angular spectrum method is applied to restore the image showing the phase of the sphere at an arbitrary spatial position. FIG. 2C is an example of a phase difference image before unwrapping of the sphere obtained by this processing. The phase of the sphere at this point is convolved with a value of 0 to $2\pi$. Therefore, for example, by applying a phase connection (unwrapping) method such as unweighted least squares or Flynn's algorithm to join portions of $2\pi$ or more, a final phase difference image of the sphere as exemplified in FIG. 2D can be obtained. It should be noted that many unwrapping methods have been proposed, and an appropriate method that does not cause phase mismatch may be appropriately selected.

Figure 3:
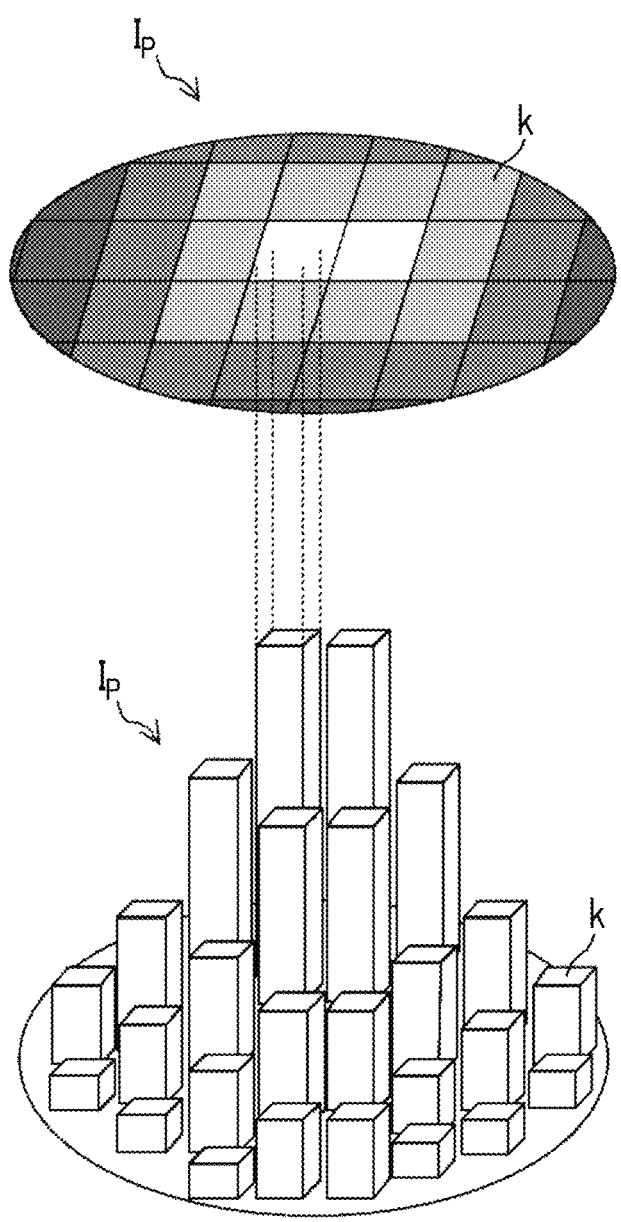
FIG. 3 is a diagram showing the concept of a phase difference image according to an embodiment of the disclosed technology.

FIG. 3 is a diagram showing the concept of a phase difference image $I_P$. In the lower part of FIG. 3, a phase difference amount at each pixel k of the phase difference image $I_P$ is three-dimensionally displayed. In the upper part of FIG. 3, the phase difference amount at each pixel k of the phase difference image $I_P$ is shown on a plane in gray scale.

Here, a phase difference amount $\theta$ in the phase difference image $I_P$ is represented by the following Equation (1) in a case where $\theta_B$ is a phase of a background (region where the sphere does not exist) existing in the same focal plane of the phase difference image $I_P$, and $\theta_S$ is a phase of a region where the sphere exists. In addition, the term "phase" in the present specification is a phase of an electric field amplitude in a case where light is regarded as an electromagnetic wave, and is used in a more general sense.

$$\theta = \theta_S - \theta_B \tag{1}$$

In addition, a phase difference amount $\theta_k$ at each pixel k of the phase difference image $I_P$ can be represented by Equation (2). Here, $n_k$ is refractive index of the sphere at the portion corresponding to each pixel k of the phase difference image $I_P$, $d_k$ is a thickness of the sphere at the portion corresponding to each pixel k of the phase difference image $I_P$, and $\lambda$ is a wavelength of the object light in the hologram optical system 10.

$$\theta_k = 2\pi \frac{n_k \cdot d_k}{\lambda} \quad (2)$$

The phase difference image of the sphere is an image showing an optical path length distribution of the object light transmitted through the sphere. Since the optical path length in the sphere corresponds to the product of the refractive index of the sphere and the thickness of the sphere, the phase difference image of the sphere includes information on the refractive index and the thickness (shape) of the sphere, as also shown in Equation (2).

Accurate information matching the actual condition of the sphere cannot be obtained from the phase difference image that is out of focus with respect to the sphere by the influence of the spread due to diffraction. Therefore, it is preferable to focus on the sphere in a case of acquiring the phase difference image from the hologram acquired by the CMOS camera 19. Here, "focusing on a sphere" means obtaining a phase difference image sliced near a center of a spherical sphere. A more accurate determination result can be obtained by determining the state of the sphere using the phase difference image focused on the sphere.

It is preferable to automate the focusing of the phase difference image without manual operation. By automating the focusing, it is possible to eliminate the arbitrariness by an operator and further shorten the processing time. The inventors have found an automatable focusing technique described below.

Figure 4:
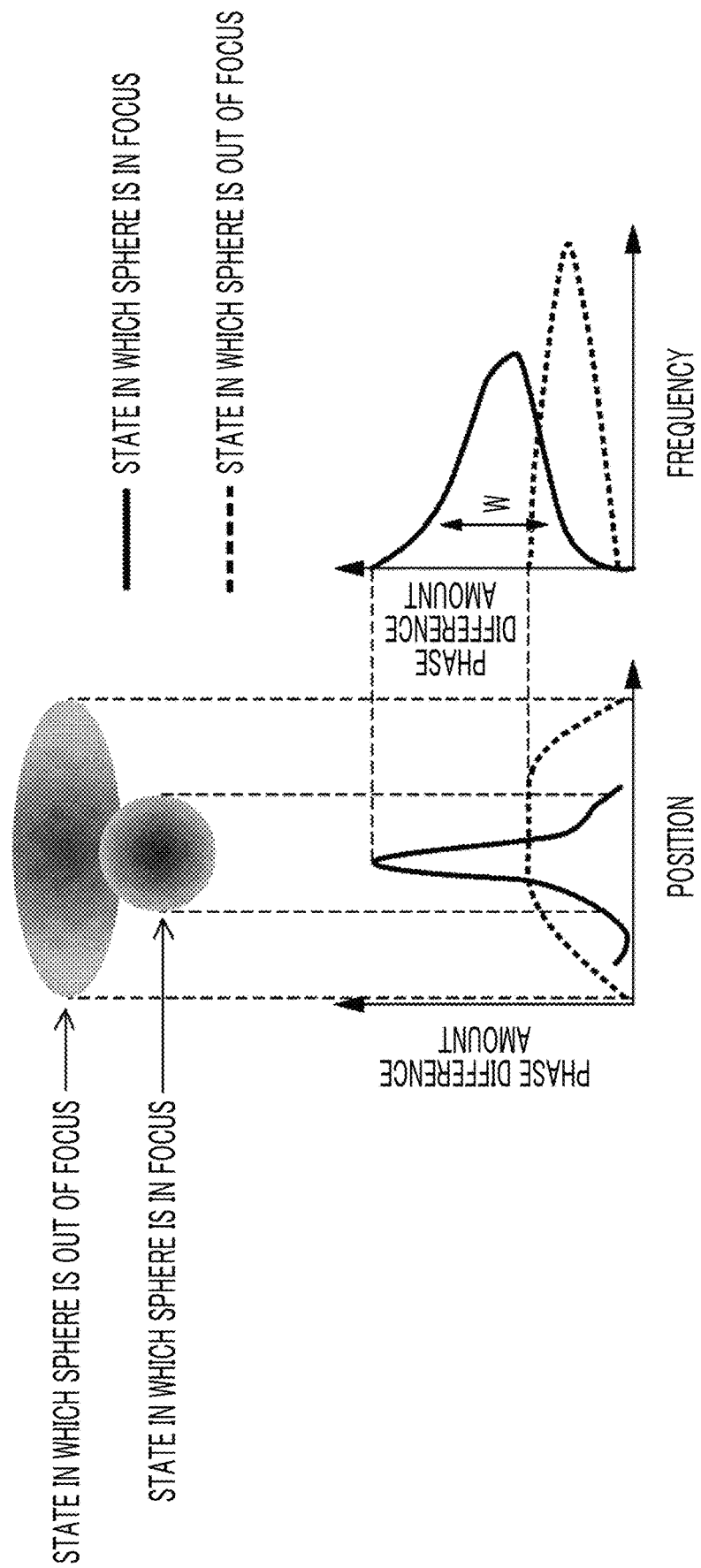
FIG. 4 is an explanatory diagram related to focusing of a phase difference image according to an embodiment of the disclosed technology.

The graph on the left side of FIG. 4 is a graph showing an example of a relationship between the position of the sphere in the plane direction and the phase difference amount in the phase difference image, in which a solid line corresponds to a state in which the sphere is in focus and a dotted line corresponds to a state in which the sphere is out of focus. In a case where the sphere is in focus, a steep peak appears at a specific position in the phase difference image. On the other hand, in a case where the sphere is out of focus, the peak is lower and smoother than the case where the sphere is in focus.

The graph on the right side of FIG. 4 is an example of a histogram of the phase difference amount in the phase difference image of the sphere, in which a solid line corresponds to a state in which the sphere is in focus and a dotted line corresponds to a state in which the sphere is out of focus. In the case where the sphere is in focus, a half-width w of a curve (variation in the phase difference amount) is relatively large, and in the case where the sphere is out of focus, the half-width w of the curve (variation in the phase difference amount) is relatively small.

Therefore, focusing can be realized by acquiring phase difference image of the sphere for each of different focal positions (slice positions), obtaining the half-width w of the curve in the histogram of the phase difference amount (variation in the phase difference amount) for each of the acquired phase difference image, and extracting the phase difference image having the maximum half-width w among the obtained half-widths w as the phase difference image focused on the sphere.

Figure 5:
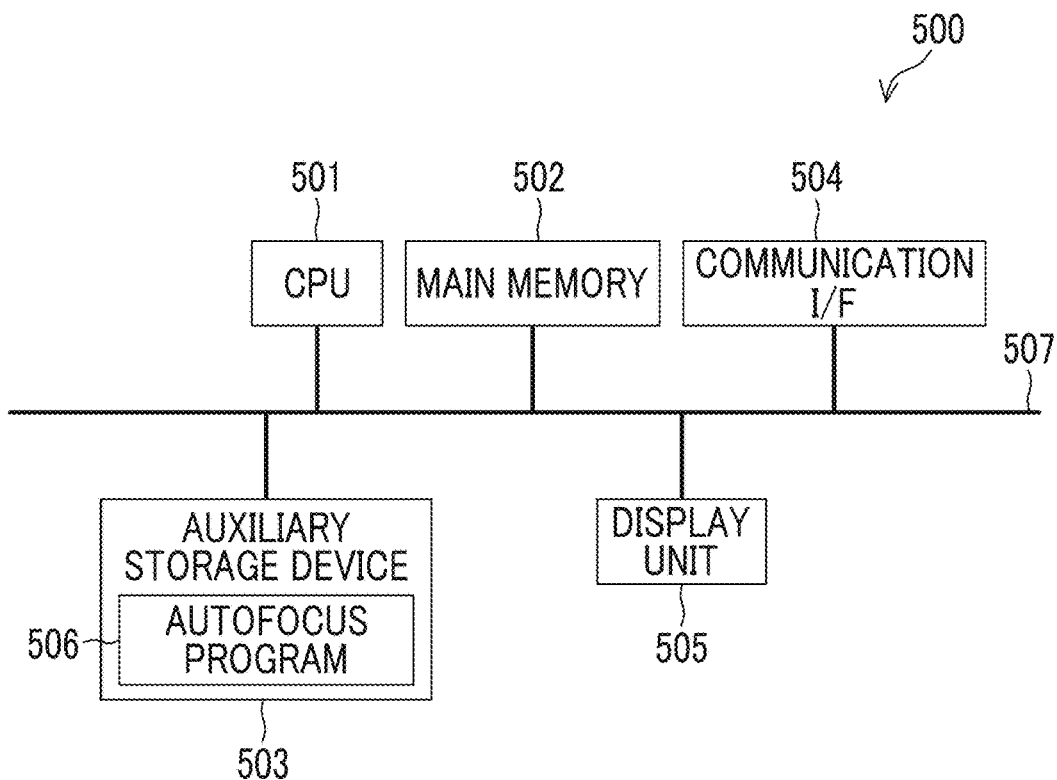
FIG. 5 is an example of a hardware configuration of a computer that performs autofocus processing according to an embodiment of the disclosed technology.

The above-described focusing can be automated using a computer. FIG. 5 is an example of a hardware configuration of a computer 500 that performs an autofocus processing for automatically performing the above-described focusing.

The computer 500 includes a central processing unit (CPU) 501, a main memory 502 as a temporary storage region, a nonvolatile auxiliary storage device 503, a communication interface (I/F) 504 for communicating with the CMOS camera 19, and a display unit 505 such as a liquid crystal display. The CPU 501, the main memory 502, the auxiliary storage device 503, the communication I/F 504, and the display unit 505 are each connected to a bus 507. The auxiliary storage device 503 houses an autofocus program 506 which describes the procedure of the above-described autofocus processing. In the computer 500, the CPU 501 executes the autofocus program 506 to perform the autofocus processing.

Figure 6:
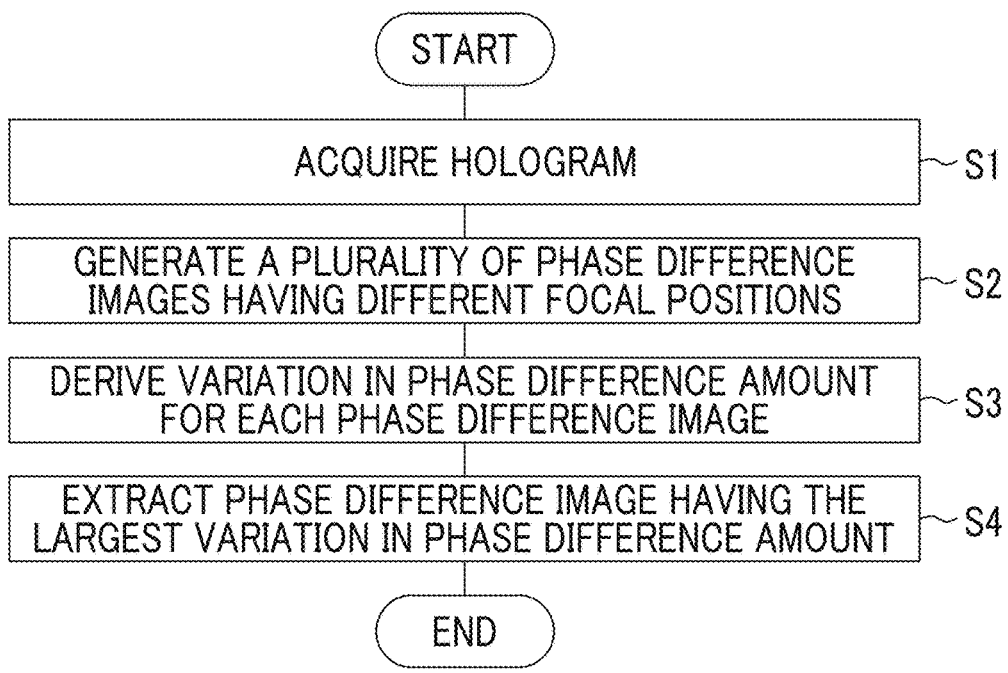
FIG. 6 is a flowchart showing an example of a flow of an autofocus processing according to an embodiment of the disclosed technology.

FIG. 6 is a flowchart showing an example of a flow of the autofocus processing performed by the computer 500.

In step S1, the CPU 501 acquires a hologram of the sphere from the CMOS camera 19.

In step S2, the CPU 501 generates a plurality of phase difference images having different focal positions (slice positions) from the acquired hologram. More specifically, a reproduction calculation is performed while sweeping a focal position (a slice position) in specified increments, and the phase image for each focal position is stocked.

In step S3, the CPU 501 derives the variation in the phase difference amount for each phase difference image for each focal position (slice position). For example, the CPU 501 may specify a sphere existence region for each phase image at each focal position (slice position), and derive a difference between the maximum value and the minimum value of the phase difference amount in the phase difference image as the variation of the phase difference amount in the phase difference image.

In step S4, the CPU 501 extracts a phase difference image having the largest variation in the phase difference amount derived in step S3 as the phase difference image focused on the sphere among the plurality of phase difference images having different focal positions (slice positions).

Figure 7:
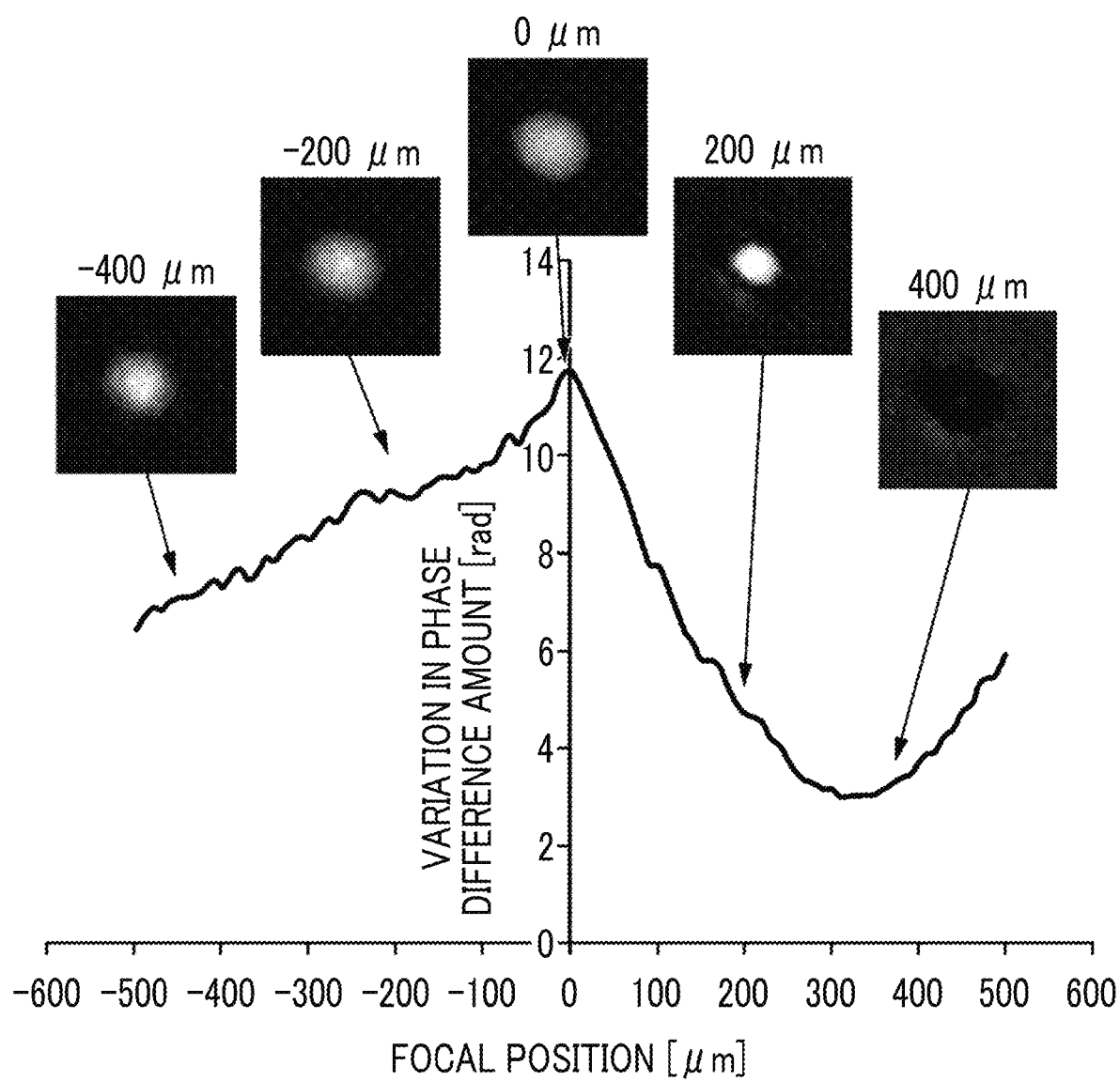
FIG. 7 is a graph showing an example of a relationship between a focal position and variation in a phase difference amount in a phase difference image of a sphere according to an embodiment of the disclosed technology.

FIG. 7 is a graph showing an example of the relationship between the focal position (slice position) and the variation in the phase difference amount in the phase difference image of the sphere. In FIG. 7, phase difference images of spheres corresponding to focal positions of −400 μm, −200 μm, 0 μm, +200 μm, and +400 μm are exemplified with a graph. In FIG. 7, a focal position in which the variation in the phase difference amount is the maximum is set to 0 μm. According to the above-described autofocus processing, the phase difference image corresponding to the focal position 0 μm in which the variation in the phase difference amount is the maximum is extracted as the focused phase difference image. In the phase difference image corresponding to the focal position 0 μm in which the variation of the phase difference amount is maximum, a contour of the sphere is the clearest.

As described above, the determination method according to the embodiment of the disclosed technology includes deriving a phase difference amount density $D_P$ obtained by dividing a total phase difference amount $\theta_A$, which is a value obtained by integrating the phase difference amounts of each of a plurality of pixels constituting the phase difference image, by the volume of the sphere.

The total phase difference amount $\theta_A$ is represented by the following Equation (3). However, s is the area of each pixel k of the phase difference image, and $v_k$ is the volume of the sphere in the portion corresponding to each pixel k of the phase difference image. As shown in Equation (3), the total phase difference amount $\theta_A$ corresponds to a value obtained by integrating the phase difference amount $\theta_k$ for each pixel of the phase difference image of the sphere for all pixels k. It should be noted that in Equation (3), $d_k$ shows a thickness of the sphere portion projected on the pixel k, and $n_k$ represents a difference in refractive index between a background culture solution and the inside of the sphere. In Equation (3), $v_k = d_k \cdot s$ is used. Here, according to Equation 3, the unit of the total phase difference amount $\theta_A$ is the scale of the area, for example, [μm²], but in a case where a comparison is not performed between the image sensors, the unit of the total phase difference amount $\theta_A$ may be simply set to [pixel] as the sum of the phase difference amount $\theta_k$ for each pixel per 1 pixel, that is, s=1 [pixel].

$$\theta_A = \sum_{k=1}^{N} \theta_k \cdot s = \frac{2\pi}{\lambda} \sum_{k=1}^{N} n_k \cdot d_k \cdot s = \frac{2\pi}{\lambda} \sum_{k=1}^{N} n_k \cdot v_k \quad (3)$$

The phase difference amount density $D_P$ is represented by the following Equation (4). However, V is the volume of the sphere. As shown in Equation (4), the phase difference amount density $D_P$ corresponds to a value obtained by dividing the total phase difference amount $\theta_A$ by a volume V of the sphere. Healthy cells are considered to maintain a constant internal refractive index different from the refractive index of the medium due to their homeostasis. On the other hand, it is considered that dead cells lose homeostasis and the internal refractive index is almost the same as that of the medium. Therefore, the phase difference amount density $D_P$ can be used as an index indicating the state of cells. Since α/λ can be treated as a constant, the multiplication of α/λ may be omitted in a case of deriving the phase difference amount density $D_P$. Here, in a case where the volume average refractive index difference $N_{ave}$ of the sphere is $N_{ave} = \Sigma n_k \cdot (v_k/V)$, since the Equation (4) is $D_P = (2\pi/\lambda) \times N_{ave}$, the phase difference density is a value obtained by normalizing the volume-averaged difference in refractive index of sphere by the length of wavelength. In the present specification, the volume V of the sphere is obtained by calculating a sphere equivalent diameter from the cross-sectional image of the phase image of the sphere. A more accurate ellipsoidal sphere is also possible.

$$D_P = \frac{\theta_A}{V} = \frac{2\pi}{\lambda} \sum_{k=1}^{N} n_k \cdot \frac{v_k}{V} \quad (4)$$

The determination method according to the embodiment of the disclosed technology includes determining the state of the sphere on the basis of the time transition of the phase difference amount density $D_P$. When the cells constituting the sphere are stem cells such as induced pluripotent stemcells (iPS) and embryonic stemcells (ES), a three-dimensional culture method in which the sphere is cultured in a suspended state in a medium can be applied. In a case where stem cells are used for regenerative medicine, differentiation induction is performed to differentiate the stem cells constituting the sphere into a specific cell such as cardiomyocytes.

The differentiation induction may include the first process of differentiating the stem cells constituting the sphere into the germ layer of any of endoderm, mesodermal, and ectoderm, and the second process of further differentiating the stem cells differentiated into the germ layer into a specific cell such as cardiomyocytes.

The sphere of iPS cells whose differentiation is induced by the three-dimensional culture method is set on the sample stage of the imaging system 1 shown in FIG. 1, and holograms of the plurality of spheres are imaged by the CMOS camera 19. A computer numerical calculation is performed on the acquired hologram of each sphere to acquire the phase difference image sliced near the center of the sphere. For the obtained phase difference image of each sphere, the phase difference amount density $D_P$ shown by Equation 4 is derived.

Figure 8:
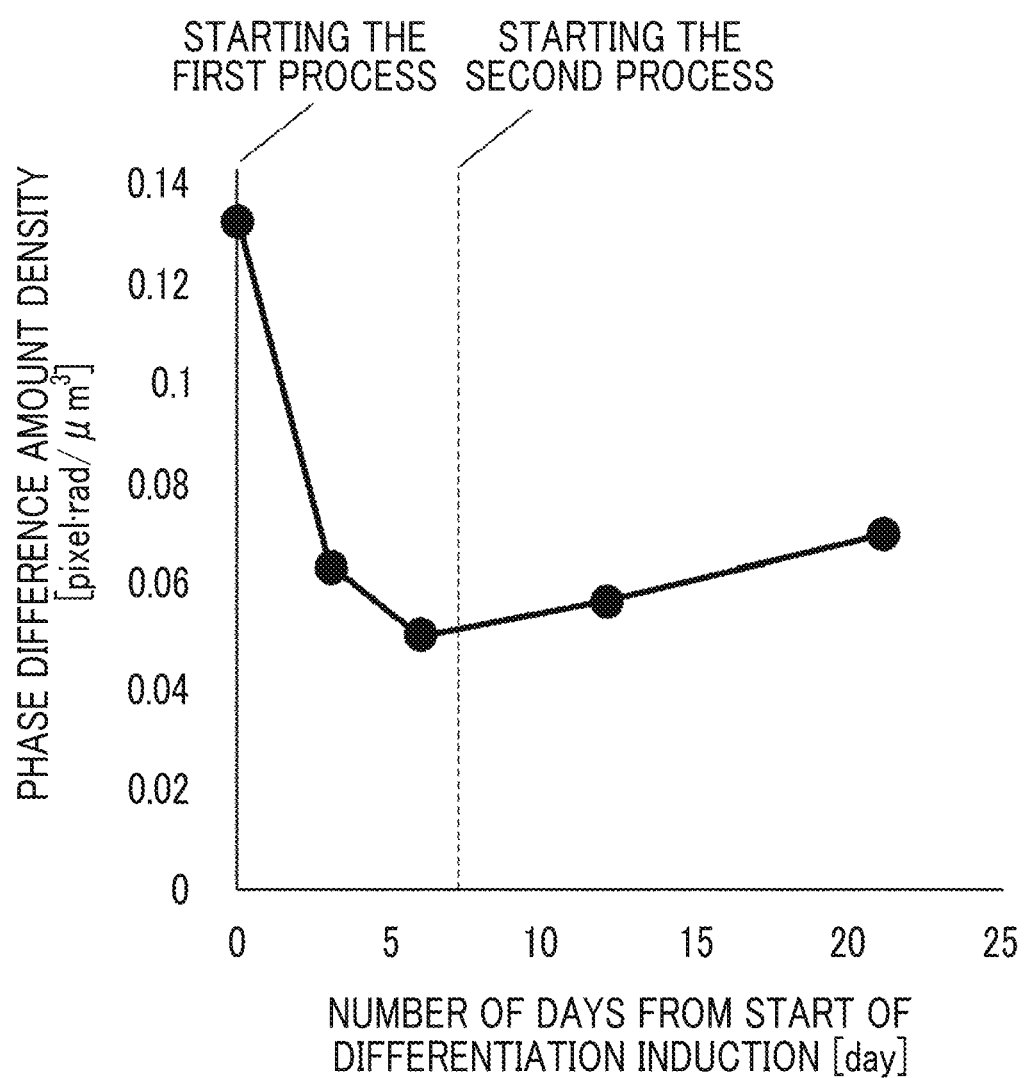
FIG. 8 is a graph showing an example of the time transition of a phase difference amount density after starting differentiation induction.

FIG. 8 is a graph showing an example of the time transition of a phase difference amount density $D_P$ after starting differentiation induction. It should be noted that each plot in the graph shown in FIG. 8 is an average value of the phase difference amount density $D_P$ acquired for a plurality of spheres. In the graph shown in FIG. 8, the day in a case where the first process of differentiating the iPS cells constituting the sphere into mesoderm is started is defined as the 0th day. The second process of further differentiating the iPS cells differentiated into mesoderm into cardiomyocytes is started from the 7th day. It should be noted that the plot on the 6th day in the graph shown in FIG. 8 is on the basis of the phase difference amount density $D_P$ acquired before starting the second process. As shown in FIG. 8, the phase difference amount density $D_P$ decreases day by day from the start of the first process to before the start of the second process (the 7th day), and then turns to increase after the start of the second process (after the 7th day).

Figure 9A:
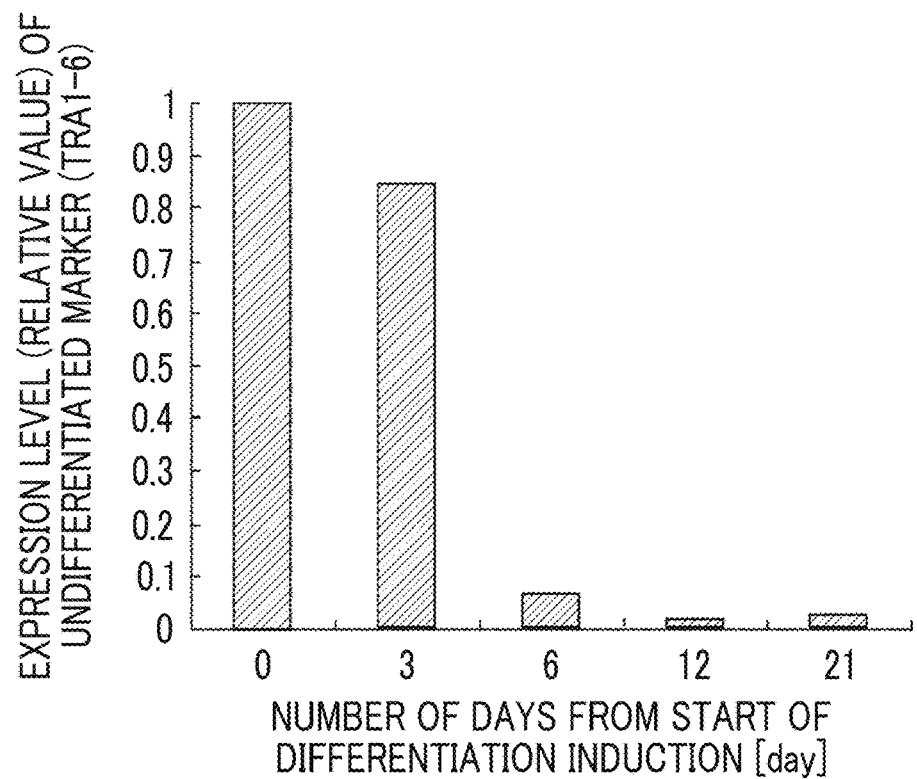
FIG. 9A is a graph showing an example of the time transition of an expression level (relative value) of an undifferentiated marker.
Figure 9B:
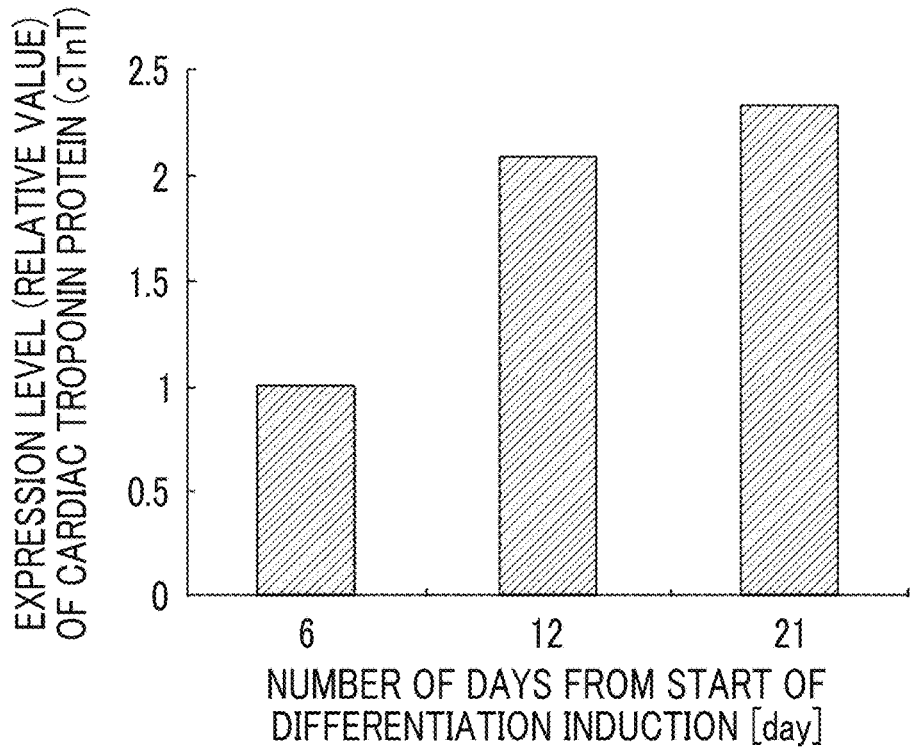
FIG. 9B is a graph showing an example of the time transition of an expression level (relative value) of a cardiac troponin protein.

FIG. 9A is a graph showing the time transition of the expression level (relative value) of an undifferentiated marker (TRA1-6) (after the 0th day) after starting the first process. FIG. 9B is a graph showing the time transition of the expression level (relative value) of the cardiac troponin protein (cTnT) (after the 7th day) after starting the second process. As shown in FIG. 9A, the expression level of the undifferentiated marker (TRA1-6) decreases day by day after starting the first process. In addition, as shown in FIG. 9B, the expression level of the cardiac troponin protein (cTnT) increases day by day after starting the second process. These results indicate that from the start of the first process until the 6th day before the start of the second process, the differentiation into mesoderm from iPS cells progresses, and after starting the second process, the differentiation into cardiomyocytes from mesoderm progresses. It should be noted that the expression level of undifferentiated markers (TRA1-6) and the cardiac troponin protein (cTnT) are measured using a commercially available general flow cytometer (ACCURI of BD) using cell suspensions collected separately.

The progression of differentiation into mesoderm from iPS cells is reflected in a decrease in the phase difference amount density $D_P$ by the 6th day after starting the first process in the graph shown in FIG. 8. In addition, the progression of differentiation into cardiomyocytes from mesoderm is reflected in an increase in the phase difference amount density $D_P$ after the 6th day in the graph shown in FIG. 8. That is, it is found that the phase difference amount density $D_P$ decreases as the differentiation into mesoderm from iPS cells progresses, and that the phase difference amount density $D_P$ increases as the differentiation into cardiomyocytes from mesoderm progresses. Accordingly, by monitoring the time transition of phase difference amount density $D_P$, it is possible to determine the state of the sphere.

In the process of differentiation from iPS cells into cardiomyocytes, the phase difference amount density $D_P$, as shown in FIG. 8, since the phase difference amount density $D_P$ shows a non-monotonous fluctuation in which it decreases once and then turns to increase, it is difficult to accurately determine the state of the sphere simply by acquiring the phase difference amount density $D_P$ at a certain temporary point. For example, it is difficult to determine whether or not the differentiation into cardiomyocytes from mesoderm is progressing smoothly or whether or not the progression of the differentiation into mesoderm from the iPS cells is delayed only from the phase difference amount density $D_P$, at a certain point after executing the second process. By monitoring the time transition of the phase difference amount density $D_P$ after the differentiation induction, it is possible to grasp the progress state of the differentiation into mesoderm from the iPS cells and the progress state of the differentiation into cardiomyocytes from mesoderm.

The determination method according to the embodiment of the disclosed technology may include determining the state of differentiation of the sphere to the germ layers on the basis of the time transition of the phase difference amount density $D_P$ after executing the first process. Specifically, the ratio of iPS cells that have differentiated into mesoderm can be estimated on the basis of a degree of change (for example, a change amount or a change rate) in the phase difference amount density $D_P$ after executing the first process (0th day and later) from the phase difference amount density $D_P$ before executing the first process (0th day or earlier).

For example, an induction efficiency E1 for the differentiation into mesoderm from the iPS cells can be estimated from the following Equation (5). In Equation (5), $D_{P1}$ is the phase difference amount density before executing the first process (0th day or earlier), and $D_{P2}$ is the phase difference amount density after executing the first process (0th day and later). $D_{PX1}$ is the minimum value of the phase difference amount density that can be reached after executing the first process. $D_{PX1}$ can be estimated from, for example, past actual data. It should be noted that briefly, the ratio of iPS cells that have differentiated into mesoderm from $D_{P1}$-$D_{P2}$ or $D_{P2}$ $D_{P1}$ may be estimated.

$$E1 = \frac{(D_{P1} - D_{P2})}{(D_{P1} - D_{PX1})} \times 100[\%] \quad (5)$$

In addition, the determination method according to the embodiment of the disclosed technology may include determining the state of differentiation into the specific cells on the basis of the time transition of the phase difference amount density $D_P$ after executing the second process. Specifically, the ratio of the cells that have differentiated into cardiomyocytes from mesoderm can be estimated on the basis of a degree of change (a change amount or a change rate) in the phase difference amount density $D_P$ after executing the second process (7th day and later) from the phase difference amount density $D_P$ before executing the first process and executing the second process (6th day).

For example, the induction efficiency E2 of the differentiation into cardiomyocytes from mesoderm can be estimated from the following Equation (6). In Equation (6), $D_{P3}$ is the phase difference amount density after executing the first process and before executing the second process (6th day), and $D_{P4}$ is the phase difference amount density after executing the second process (7th day and later). $D_{PX2}$ is the maximum value of the phase difference amount density that can be reached after executing the second process. $D_{PX2}$ can be estimated from, for example, past actual data. It should be noted that briefly, the ratio of the cells that have differentiated into cardiomyocytes from mesoderm may be estimated by $D_{P4}$-$D_{P3}$ or $D_{P4}/D_{P3}$.

$$E2 = \frac{(D_{P4} - D_{P3})}{(D_{PX2} - D_{P3})} \times 100[\%] \quad (6)$$

Figure 10:
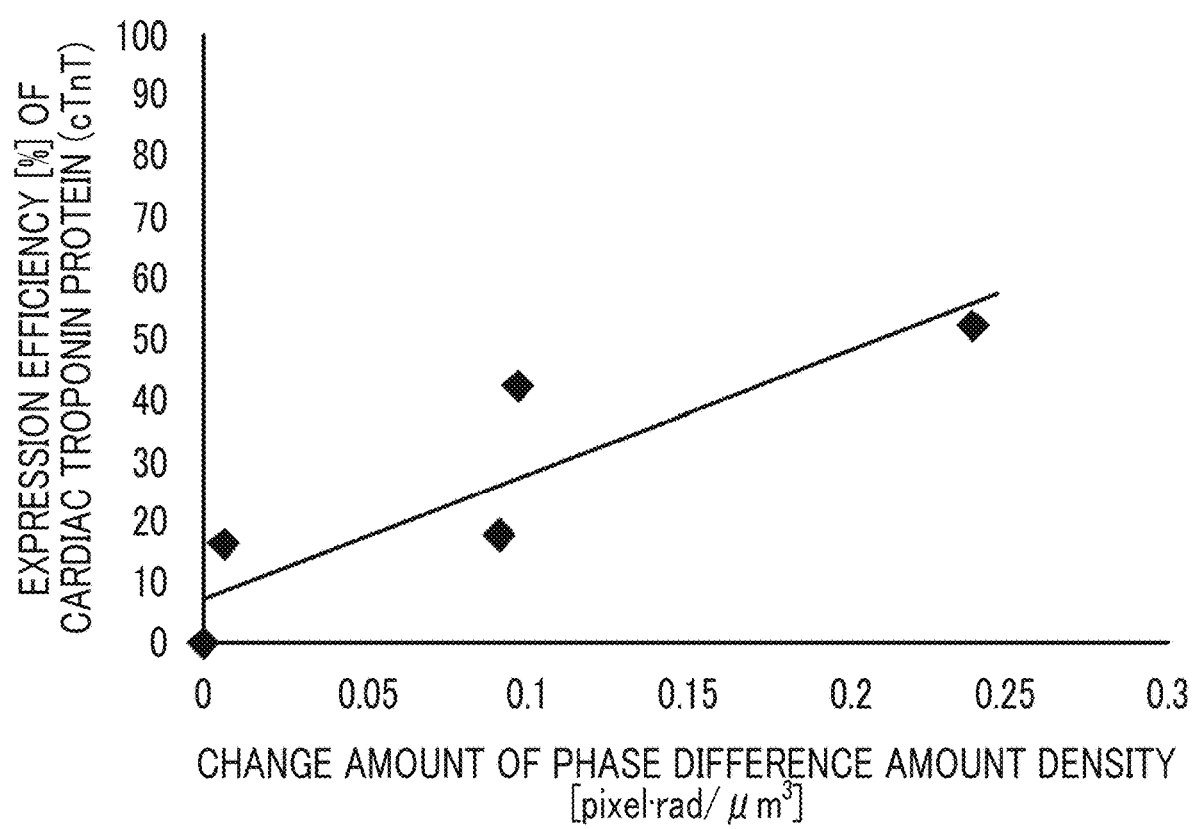
FIG. 10 is a diagram showing an example of a calibration curve showing a relationship between a change amount of the phase difference amount density and an expression efficiency of a cardiac troponin protein.

In addition, as shown in FIG. 10, a calibration curve showing a relationship between the change amount in the phase difference amount density $D_P$ after executing the second process (7th day and later) and the expression efficiency of the cardiac troponin protein (cTnT) may be acquired, and the progress state of differentiation into the cardiomyocytes may be estimated from the phase difference amount density $D_P$ acquired after executing the second process (7th day and later) and the calibration curve.

The determination method according to the embodiment of the disclosed technology may include determining the lot to be determined including a plurality of spheres on the basis of the time transition of the phase difference amount density $D_P$ from the execution of the first process to the lapse of a predetermined period after the execution of the second process.

Figure 11:
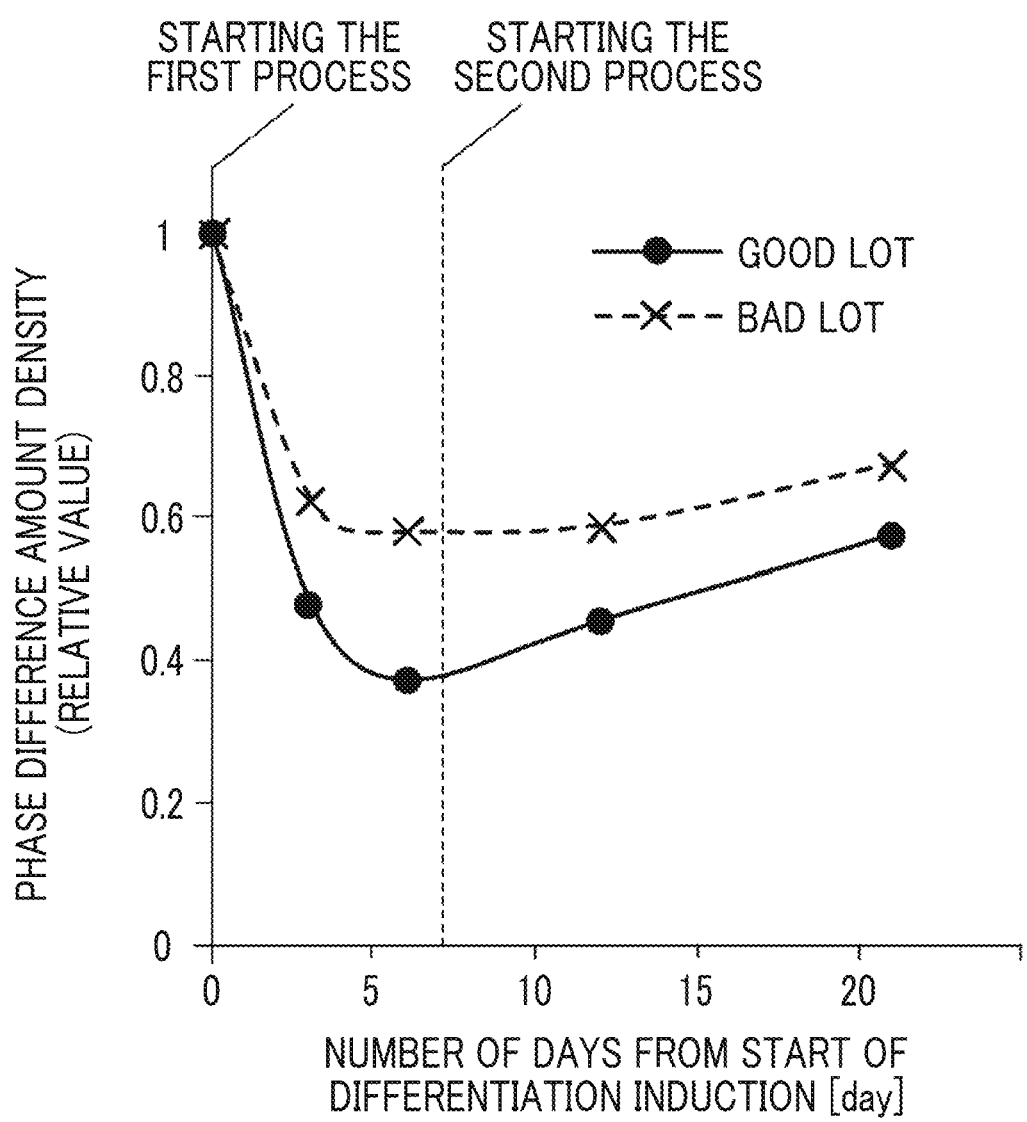
FIG. 11 is a graph showing the time transition of a phase difference amount density acquired for a good lot and a bad lot.

FIG. 11 is a graph showing the time transition of the phase difference amount density $D_P$ acquired for a good lot (solid line) in which the progression of the differentiation into cardiomyocytes is smooth and a bad lot (dotted line) in which the progression of the differentiation to cardiomyocytes is not smooth. It should be noted that in the bad lot, no pulsation has been confirmed from cardiomyocytes after the differentiation. In FIG. 11, each plot is a relative value of the average value of the phase difference amount density $D_P$ acquired for each of a plurality of spheres belonging to the lot, with 0th day set to 1. As shown in FIG. 11, a clear difference has been confirmed in the time transition of the phase difference amount density $D_P$ between the good lot and the bad lot. That is, in the bad lot, the change amount in the phase difference amount density $D_P$ is smaller than that of the good lot.

Figure 12A:
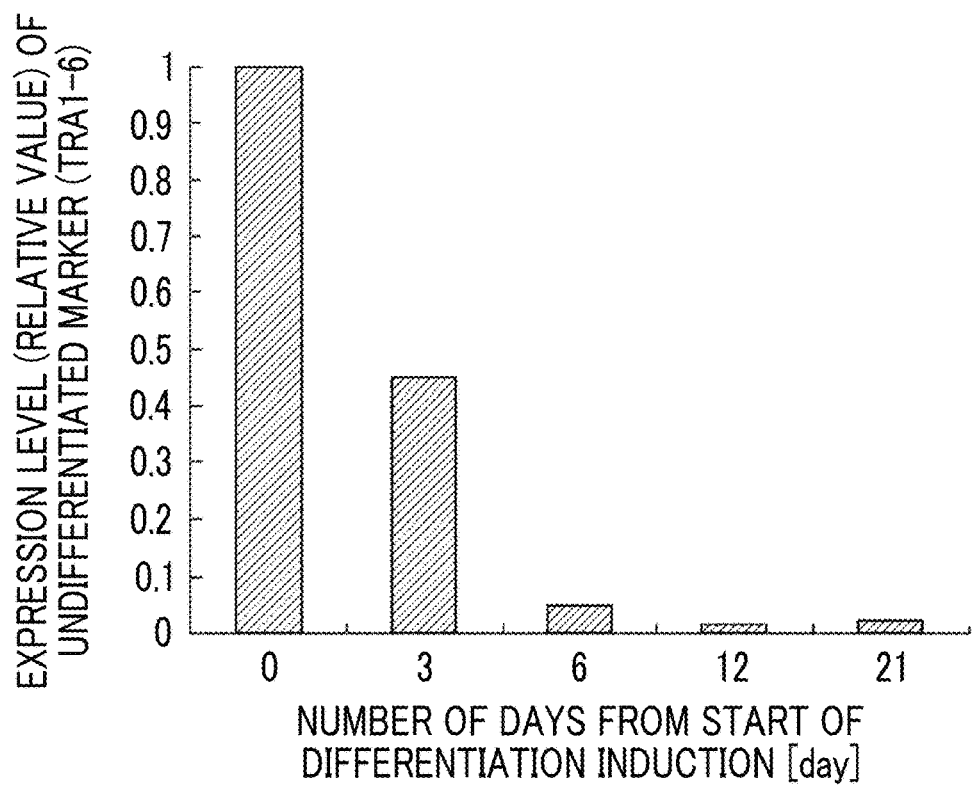
FIG. 12A is a graph showing the time transition of an expression level (relative value) of an undifferentiated marker acquired for a bad lot.
Figure 12B:
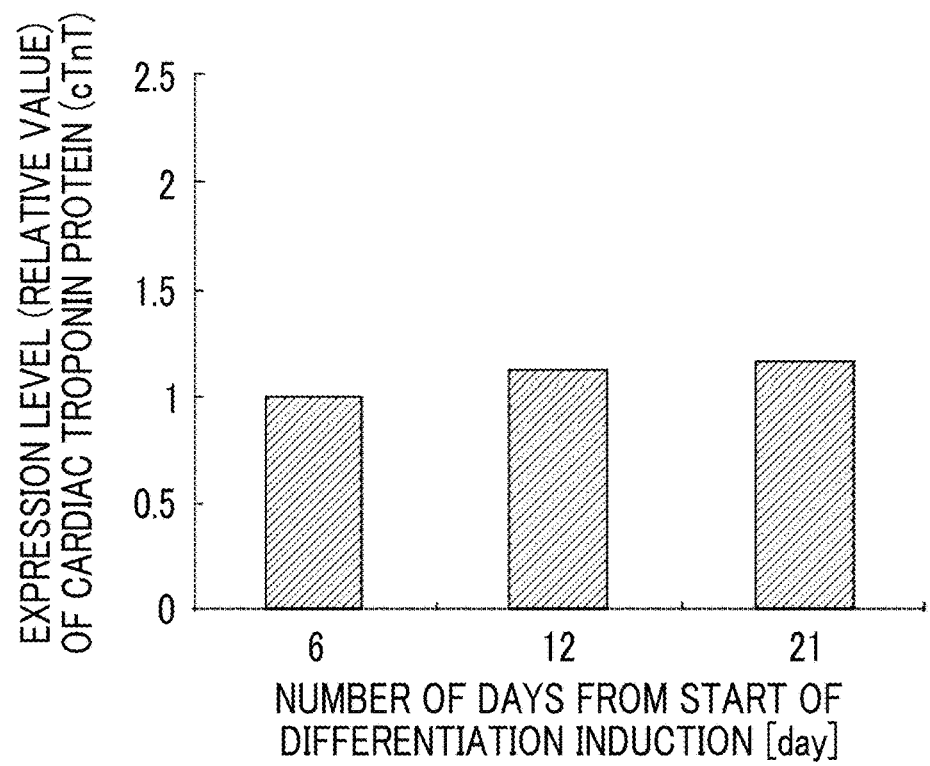
FIG. 12B is a graph showing the time transition of an expression level (relative value) of a cardiac troponin protein acquired for a bad lot.

FIG. 12A is a graph showing the time transition of an expression level (relative value) of an undifferentiated marker (TRA1-6) acquired for the bad lot. FIG. 12B is a graph showing the time transition of an expression level (relative value) of a cardiac troponin protein (cTnT) acquired for the bad lot. In the bad lot, as shown in FIG. 12A, it is confirmed that the expression level of the undifferentiated marker (TRA1-6) decreases day by day, confirming that the differentiation into mesoderm is progressing. However, in the bad lot, as shown in FIG. 12B, it is confirmed that the expression level of cardiac troponin protein (cTnT) is hardly increased, and the progression of the differentiation into cardiomyocytes is not smooth. In the bad lot, the fact that the progression of the differentiation into cardiomyocytes is not smooth is reflected, in the graph shown in FIG. 11, in the fact that the change in the phase difference amount density $D_P$ of the bad lot is smaller than that of the good lot. This shows that it is possible to perform the determination for the lot to be determined on the basis of the time transition of the phase difference amount density $D_P$.

For example, the determination for the lot to be determined may be performed on the basis of a degree of deviation from reference data of the time transition of the phase difference amount density $D_P$, from the execution of the first process to the lapse of the predetermined period after executing of the second process, acquired for the lot to be determined. That is, the determination of the lot to be determined may be performed on the basis of how far the time transition of the phase difference amount density $D_P$ acquired for the lot to be determined deviates from the reference data.

In a case where the result of differentiation induction corresponding to the time transition of the phase difference amount density $D_P$ is known, the time transition of the phase difference amount density $D_P$ can be used as reference data. For example, the time transition of the phase difference amount density $D_P$ acquired for a good lot in which the progression of differentiation into mesoderm and differentiation to cardiomyocytes is confirmed to be smooth can be used as the reference data. In this case, for example, in a case where the magnitude of the deviation of the time transition of the phase difference amount density $D_P$ acquired for the lot to be determined from the reference data exceeds a threshold value, the lot to be determined may be determined as a bad lot, and in a case where the magnitude of the deviation from the reference data is less than the threshold value, the lot to be determined may be determined as a good lot. For example, the sum of squares of residuals may be used as an index value indicating the magnitude of the deviation. In addition, the time transition of phase difference amount density $D_P$ acquired for a plurality of past culture lots that averaged can also be used as reference data.

For example, a virtual time transition derived on the basis of the time transition of the phase difference amount density $D_P$ in the good lot may be used as reference data. For example, the time transition corresponding to the first assumed case shown in FIG. 13 can be used as the reference data. The first assumed case is a case in which the progression of the differentiation into mesoderm is smooth, and subsequent differentiation into cardiomyocytes is slightly delayed as compared with the standard case, but there is no problem in myocardial function. In a case where the time transition of phase difference amount density $D_P$ to be determined lot indicates the same pattern as the first assumed case, the lot to be determined may be determined as a good lot. In a case where the progression of differentiation into cardiomyocytes in the time transition of the phase difference amount density $D_P$ of the lot to be determined is further delayed than in the first assumed case (that is, in a case where the phase difference amount density $D_P$ on and after the 7th day is lower than the first assumed case), the lot to be determined may be determined to be a bad lot.

Figure 13:
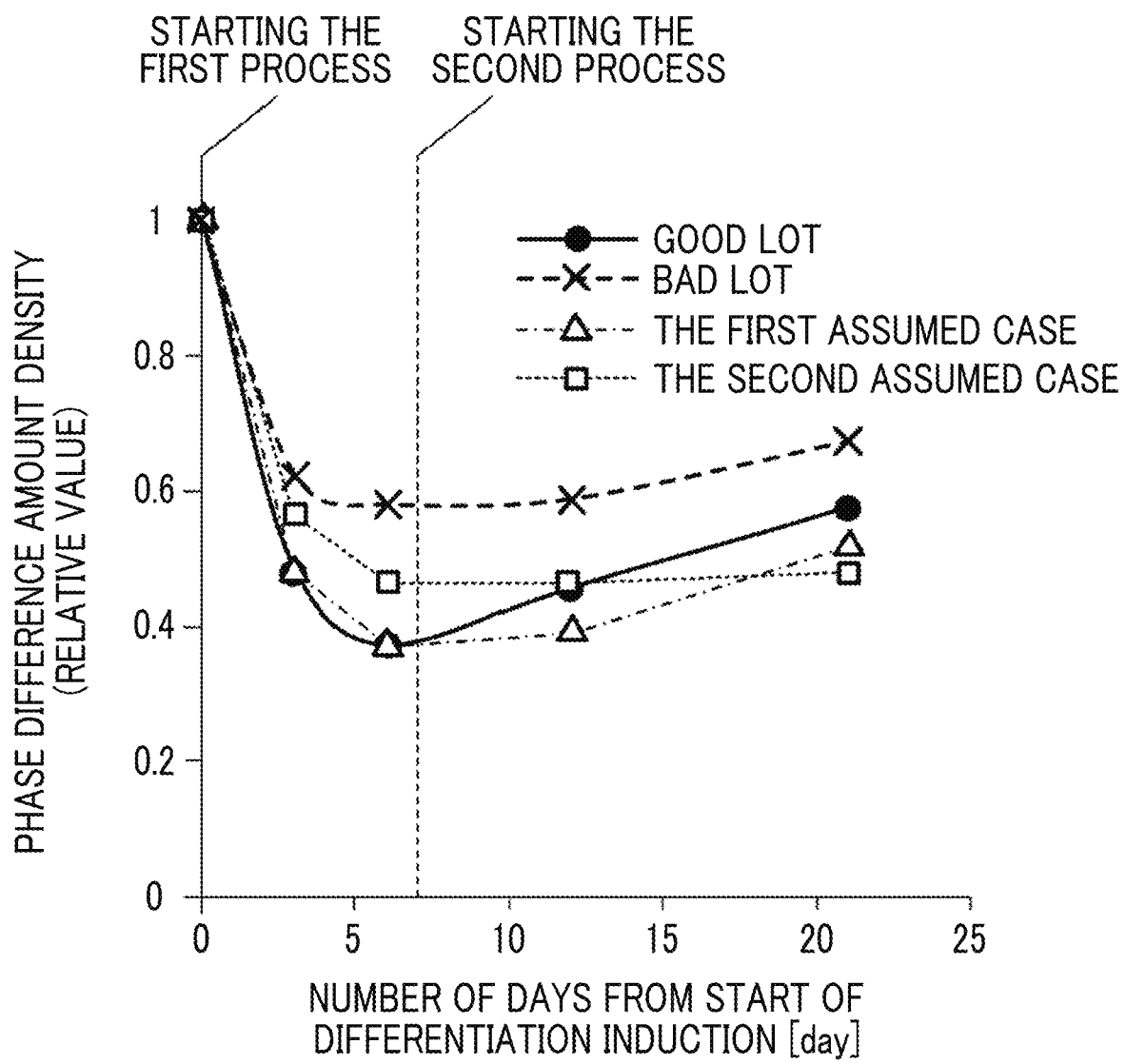
FIG. 13 is a graph showing an example of the time transition of a phase difference amount density in the first and second assumed cases.

In addition, for example, the time transition corresponding to the second assumed case shown in FIG. 13 can be used as the reference data. The second assumed case is a case in which the differentiation into mesoderm is insufficient, purity of cardiomyocytes is low, and myocardial function is also insufficient. In a case where the time transition of phase difference amount density $D_P$ to be determined lot indicates the same pattern as the second assumed case, the lot to be determined may be determined as a bad lot.

Figure 14:
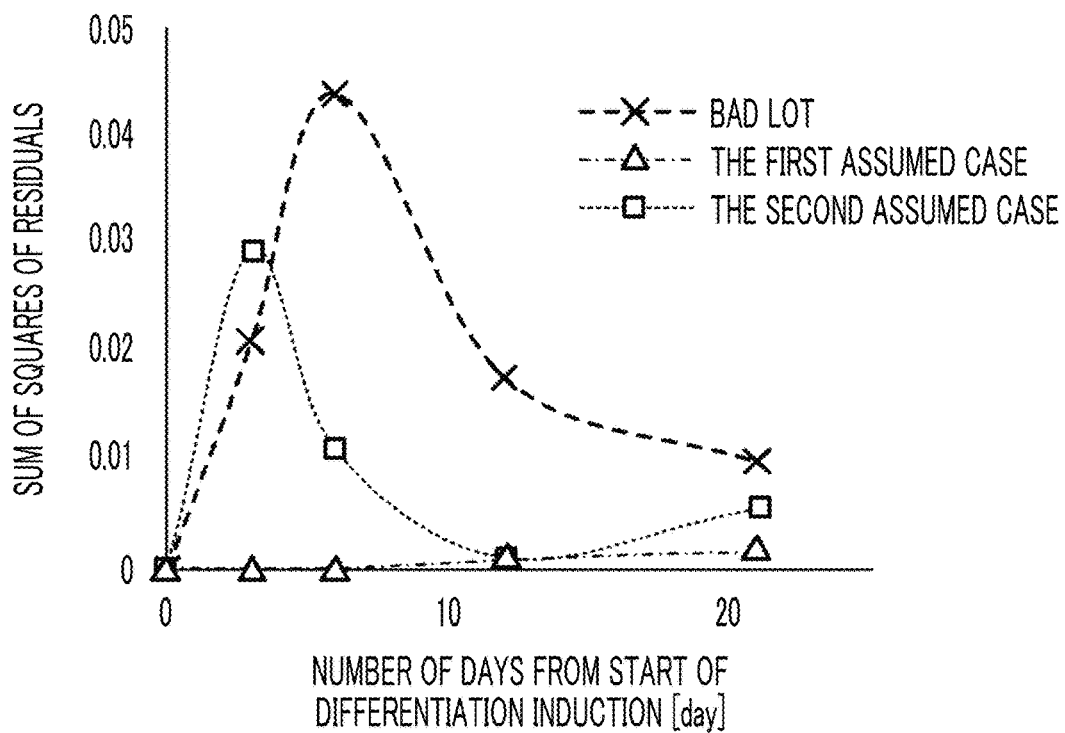
FIG. 14 is a graph showing an example of the time transition of the sum of squares of residuals with respect to a good lot in a bad lot, the first assumed case, and the second assumed case.

FIG. 14 is a graph showing the time transition of the sum of squares of residuals with respect to a good lot in a bad lot, the first assumed case, and the second assumed case. For example, in a case where the sum of squares of residuals with respect to the good lot of the phase difference amount density $D_P$ acquired for the lot to be determined at a certain time exceeds a line of the first assumed case in the graph shown in FIG. 14, the lot to be determined may be determined as a bad lot.

Since the process of differentiation induction of stem cells requires a relatively long time and it is difficult to create appropriate samples with good reproducibility as reference data, it is not easy to prepare reference data based on actual measurement. According to the determination method of the embodiment of the disclosed technology that performs the determination of the lot to be determined on the basis of the time transition of the phase difference amount density $D_P$, as described above, reference data used for determination can be virtually set, and appropriate determination can be performed without preparing the reference data based on the actual measurement.

Figure 15:
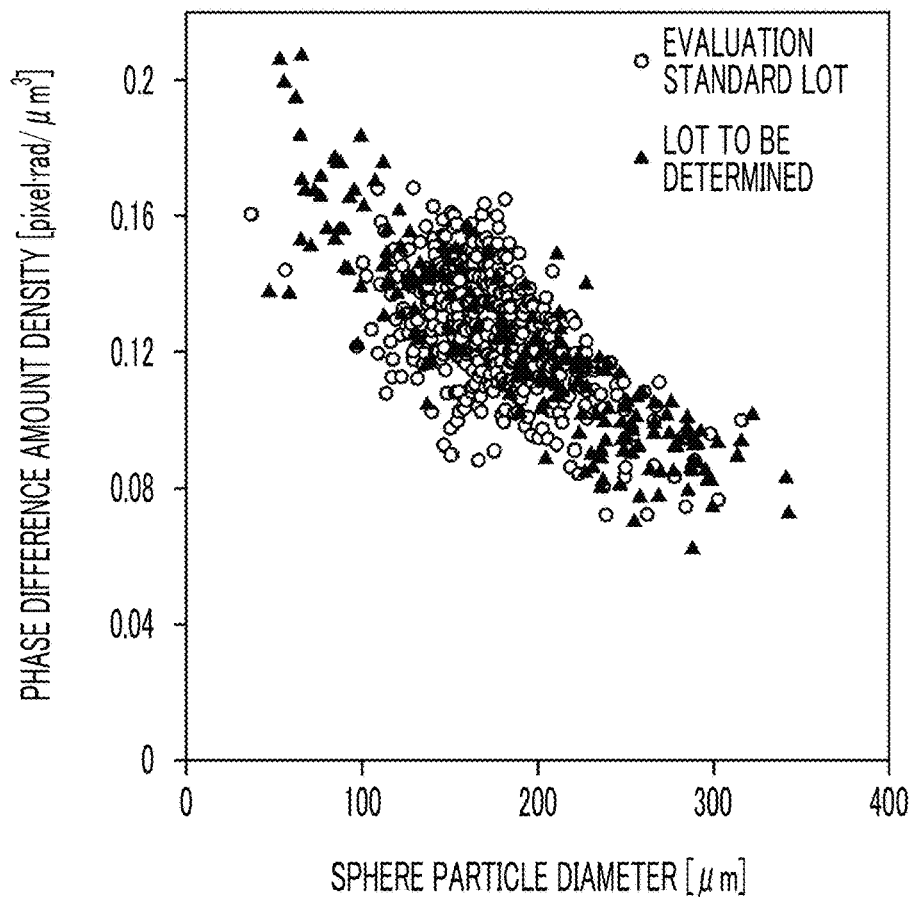
FIG. 15 is a graph showing an example of a correlation between a sphere particle diameter and the phase difference amount density acquired for a plurality of spheres included in a lot to be determined and an evaluation standard lot.

FIG. 15 is a graph showing an example of a correlation between a sphere particle diameter and the phase difference amount density $D_P$ acquired for a plurality of spheres included in a lot to be determined and an evaluation standard lot. It should be noted that a culture lot having a relatively small variation in the sphere particle diameter can be applied as an evaluation standard lot. For example, a culture lot in which the standard deviation of the sphere particle diameter in the lot is equal to or less than a predetermined value may be applied as an evaluation standard lot.

As shown in FIG. 15, it is found that as the sphere particle diameter increases, there is a tendency that the phase difference amount density $D_P$ decreases. Sphere particle diameter dependency in the phase difference amount density $D_P$ can be considered to represent the characteristics of a cell line, and the characteristic of a three-dimensional culture process and a differentiation induction process. Specifically, due to a gas density and a permeability of the inducing factor, a sphere having a small particle diameter tends to be uniform in the progress of differentiation, while a sphere having a large particle diameter tends to be uneven in the progress of differentiation, and size density of a cell density in the sphere is different according to the culture and differentiation induction process. Accordingly, it is considered that such factors cause the phase difference amount density $D_P$ to have the sphere particle diameter dependency.

Since the phase difference amount density $D_P$ is assumed to function as an index value related to the refractive index of the sphere, in a case where the phase difference amount density $D_P$ has the sphere particle diameter dependency, it may be difficult to appropriately determine the state of the sphere based on the time transition of the phase difference amount density $D_P$. Accordingly, it is preferable to suppress the sphere particle diameter dependency of the phase difference amount density $D_P$. A method for suppressing the sphere particle diameter dependency of the phase difference amount density $D_P$ includes a method that a correction coefficient corresponding to a sphere particle diameter distribution of the sphere is derived, and a correction value of the phase difference amount density $D_P$ is derived using the correction coefficient. This method will be described in detail below.

Figure 16A:
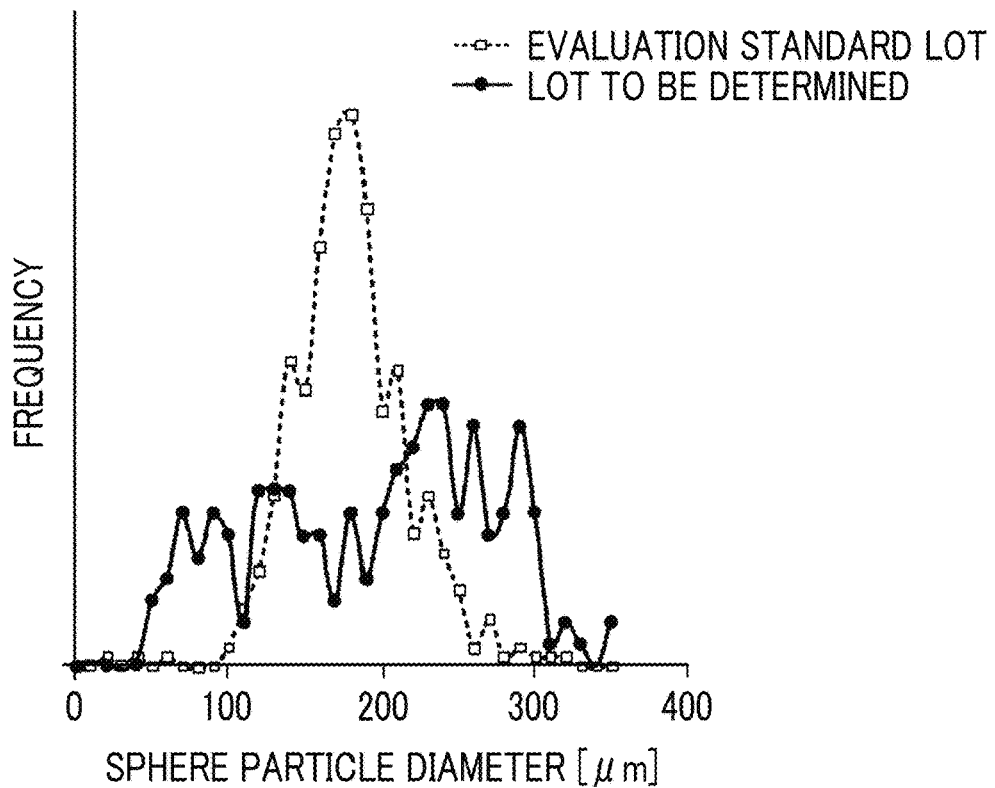
FIG. 16A is a frequency distribution of a sphere particle diameter acquired for a plurality of spheres included in a lot to be determined and an evaluation standard lot.
Figure 16B:
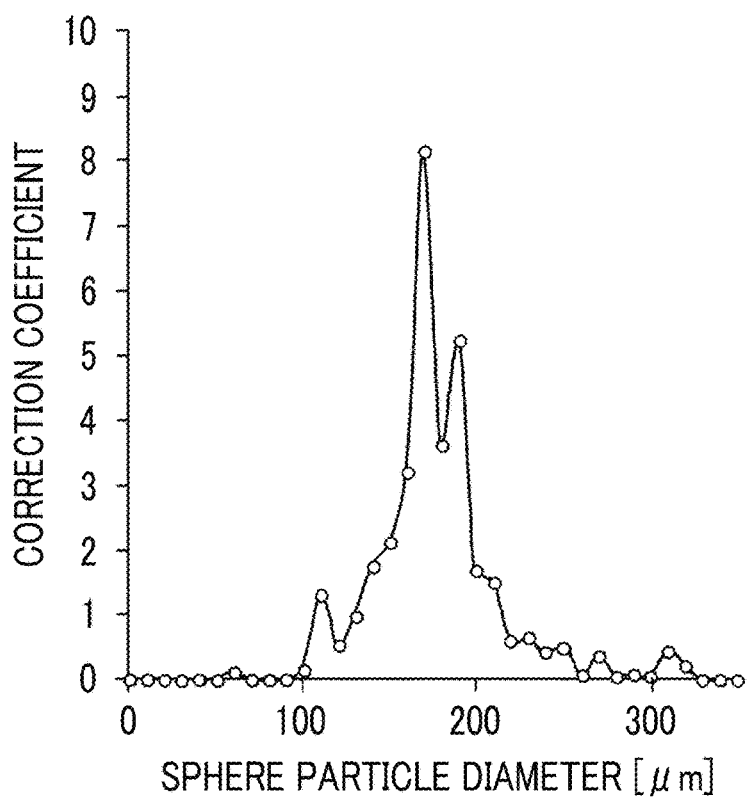
FIG. 16B is a diagram showing a correction coefficient derived for each class of a frequency distribution shown in FIG. 16A.

FIG. 16A is a frequency distribution of a sphere particle diameter acquired for a plurality of spheres included in a lot to be determined and an evaluation standard lot. First, a value obtained by dividing the frequency in each class of the frequency distribution of the sphere particle diameter in the evaluation standard lot by the frequency in the corresponding class of the frequency distribution of the sphere particle diameter in the lot to be determined is derived as a correction coefficient, respectively. FIG. 16B is a diagram showing a correction coefficient derived for each class of a frequency distribution shown in FIG. 16A. For example, in a case where a frequency in class A of the frequency distribution in the evaluation standard lot is a, and a frequency in class A of the frequency distribution in the lot to be determined is b, a correction coefficient $K_A$ for the class A is a/b.

Next, the phase difference amount density $D_P$ acquired for each of a plurality of spheres that are included in the lot to be determined is multiplied by a corresponding correction coefficient to derive a correction value of the phase difference amount density $D_P$ for each sphere. That is, the spheres belonging to a class with the lot to be determined is multiplied by the correction coefficient derived for the class, the phase difference amount density $D_P$ acquired for the sphere. Thus, the correction value of the phase difference amount density $D_P$ of the sphere is obtained. For example, a correction value of a phase difference amount density $D_{PA}$ of a sphere belonging to class A of the frequency distribution is the $K_A D_{PA}$ in a case where the correction coefficient in class A is $K_A$. As described above, by correcting the phase difference amount density of the lot to be determined, the lot to be determined can be treated as having the same sphere particle diameter distribution as the evaluation standard lot, so that lot determination based on the phase difference amount density can be properly performed.

The determination method according to the embodiment of the disclosed technology may include, as described above, deriving a correction value of the phase difference amount density $D_P$ for each of a plurality of spheres that are included in the lot to be determined, and performing the determination for the lot to be determined on the basis of the time transition of the average value of the derived correction value in the plurality of spheres. By using the correction value of the phase difference amount density $D_P$, since the sphere particle diameter dependency in the phase difference amount density $D_P$ is suppressed, it is possible to make the determination for the lot to be determined more accurately.

In the above description, the case of suppressing the sphere particle diameter dependency of the phase difference amount density $D_P$ in the determination based on the time transition of the phase difference amount density $D_P$ has been exemplified, but the lot to be determined may be determined using the sphere particle diameter dependency of the phase difference amount density $D_P$. For example, an index value indicating the correlation between the phase difference amount density $D_P$ and the sphere particle diameter may be derived for a plurality of spheres included in the lot to be determined, and the lot to be determined may be determined on the basis of the time transition of the index value.

Figure 17:
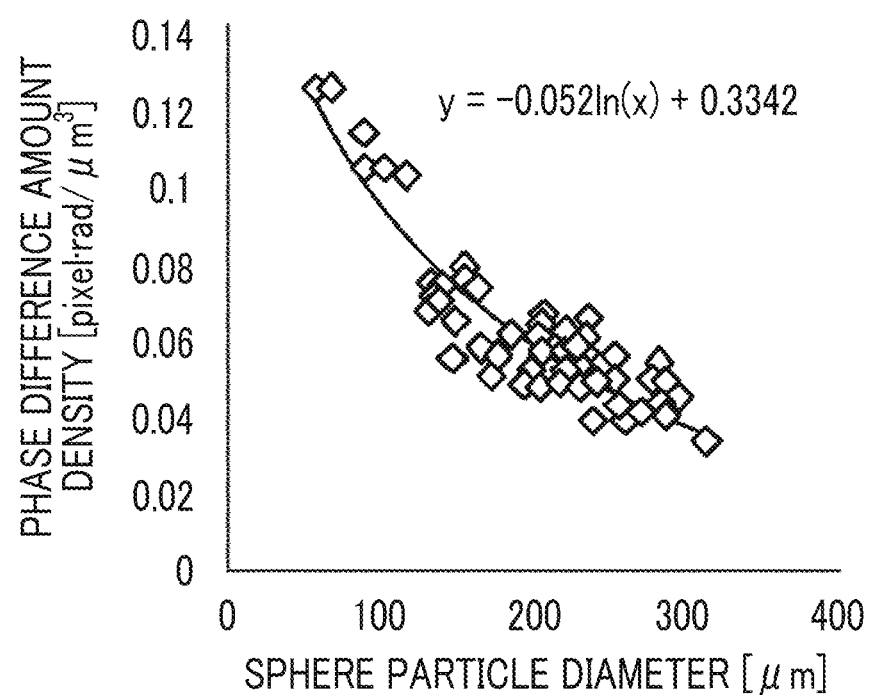
FIG. 17 is a graph showing an example of a correlation between a sphere particle diameter and a phase difference amount density at a certain time point after starting differentiation induction.

FIG. 17 is a graph showing an example of the correlation between the sphere particle diameter and the phase difference amount density $D_P$ at a certain time point after starting differentiation induction. The correlation between the sphere particle diameter and the phase difference amount density $D_P$ shown in FIG. 17, for example, can be fitted by the function shown in the following Equation (7). That is, the correlation between the sphere particle diameter and the phase difference amount density $D_P$ can be represented by an approximate equation by the function shown in Equation (7). X in Equation (7) is a sphere particle diameter, Y is the phase difference amount density $D_P$, and A and B are constants.

$$Y = A \cdot ln(X) + B \qquad (7)$$

Figure 18:
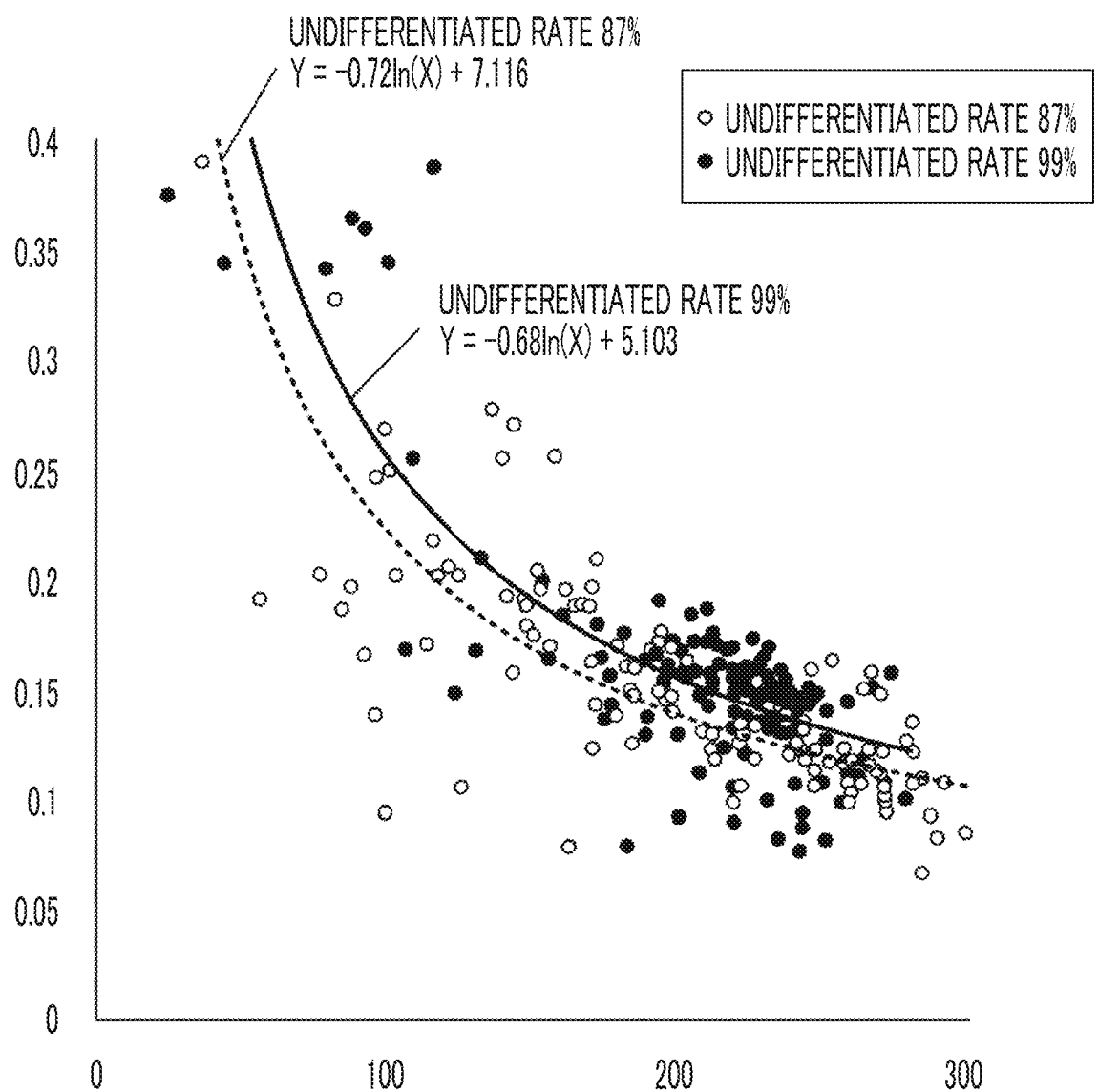
FIG. 18 is a graph showing an example of a correlation between a sphere particle diameter and a phase difference amount density.

The correlation shown in FIG. 17 can be represented as Y=−0.052 lnX+0.03342 as a result of fitting by the function shown in the following Equation (7). The constant A in Equation (7) can be used as an index value indicating the correlation between the sphere particle diameter and the phase difference amount density $D_P$. Here, FIG. 18 is a graph showing the correlation between the sphere particle diameter and the phase difference amount density $D_P$ acquired for a plurality of spheres included in each of two lots in which the ratio (hereinafter referred to as undifferentiated rate) of iPS cells maintaining an undifferentiated state within the lot is 87% and 99%, respectively. As shown in FIG. 18, since the correlation between the sphere particle diameter and the phase difference amount density $D_P$ changes according to the undifferentiated rate of the cells, it is considered possible to perform the determination for the lot to be determined by monitoring the time transition of the constant A after starting differentiation induction.

Figure 19:
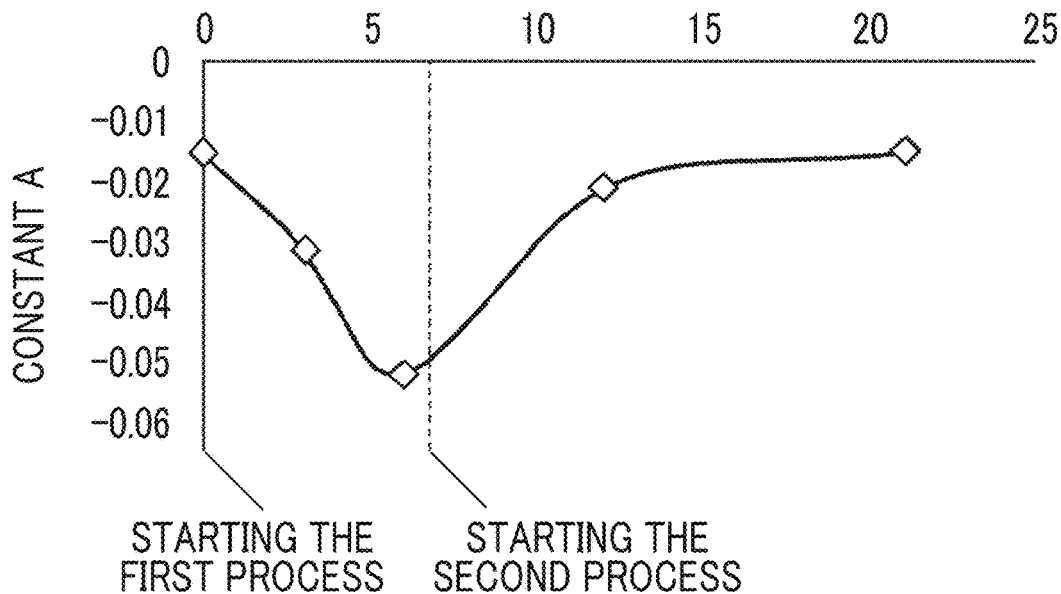
FIG. 19 is a graph showing an example of the time transition of a constant A after starting differentiation induction.

FIG. 19 is a graph showing an example of the time transition of the constant A after starting differentiation induction. Similar to the graph shown in FIG. 8, the constant A has an extreme value on the 6th day, which is the start date of the second process. This indicates that it is possible to accurately determine the lot to be determined by monitoring the time transition of the constant A.

In addition, the correlation between the sphere particle diameter and the phase difference amount density $D_P$ shown in FIG. 17, for example, can be fitted by the function shown in the following Equation (8). That is, the correlation between the sphere particle diameter and the phase difference amount density $D_P$ can be represented by an approximate equation by the function shown in Equation (8). X in Equation (8) is a sphere particle diameter, Y is the phase difference amount density $D_P$, and F and G are constants.

$$Y = F \cdot \exp(G \cdot X) \qquad (8)$$

The constant G in Equation (8) can be used as an index value indicating the correlation between the sphere particle diameter and the phase difference amount density $D_P$. Since the correlation between the sphere particle diameter and the phase difference amount density $D_P$ is assumed to change according to the progress state of differentiation of the stem cells, it is possible to perform the determination for the lot to be determined by monitoring the time transition of the constant G after starting differentiation induction.

Figure 20:
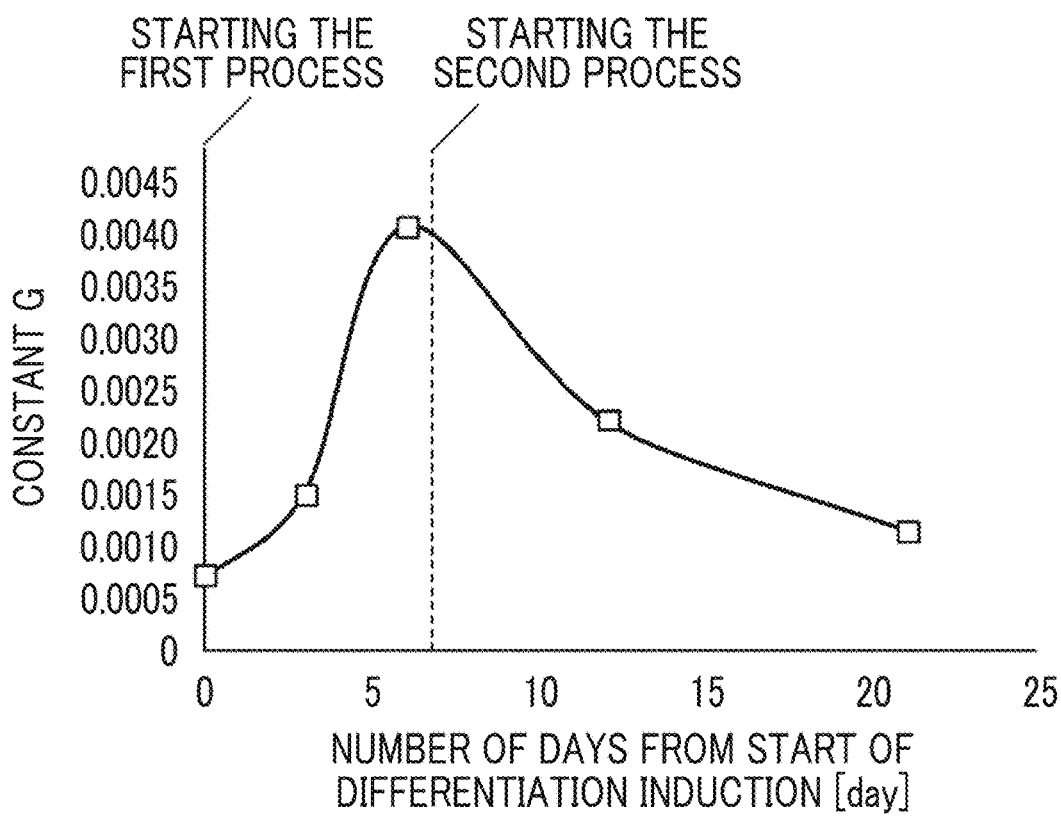
FIG. 20 is a graph showing an example of the time transition of a constant G after starting differentiation induction.

FIG. 20 is a graph showing an example of the time transition of the constant G after starting differentiation induction. Similar to the graph shown in FIG. 8, the constant G has an extreme value on the 6th day, which is the start date of the second process. This indicates that it is possible to accurately determine the lot to be determined by monitoring the time transition of the constant G.

As described above, the determination method according to the embodiment of the disclosed technology may perform the determination for the lot to be determined on the basis of the time transition of the index value indicating the correlation between the phase difference amount density $D_P$ and the sphere particle diameter for a plurality of the spheres included in the lot to be determined. Thus, by using the correlation between the phase difference amount density $D_P$ and the sphere particle diameter, it is possible to make the determination for the lot to be determined more accurately.

As is clear from the above description, according to the determination method of the embodiment of the disclosed technology, the state of the aggregate of a plurality of cells formed by three-dimensional culture can be determined non-destructively and easily. It should be noted that in the present embodiment, a case where analysis is performed with a phase difference amount density for a three-dimensional embryoid body (spheroid) form is exemplified, but the state of the cell may be determined by using the time transition of the phase difference amount density acquired for the two-dimensional plane cultured cell.

EXPLANATION OF REFERENCES

1: imaging system
10: hologram optical system
11: laser light source
12: beam splitter
13: collimating lens
14: sample
15: objective lens
17: imaging lens
18: beam splitter
19: CMOS camera
20: optical fiber
21: collimating lens
34: dichroic mirror
500: computer
502: main memory
503: auxiliary storage device
504: communication interface
505: display unit
506: autofocus program
507: bus
$D_P$: phase difference amount density
$I_P$: phase difference image
$\theta$: phase difference amount
$\theta_B$: phase of background
$\theta_S$: phase of region where sphere exist
$\theta_A$: total phase difference amount
$\theta_k$: phase difference amount per 1 pixel
V: volume of sphere
$v_k$: volume of sphere in portion corresponding to each pixel k of phase difference image
k: pixel
w: half-width of curve

What is claimed is:

1. A determination method comprising:
   generating a phase difference image of an aggregate of a plurality of cells from a hologram obtained by imaging the aggregate;
   deriving a phase difference amount density by dividing a total phase difference amount that is a value obtained by integrating a phase difference amount of each of a plurality of pixels constituting the phase difference image by a volume of the aggregate; and
   determining a state of the aggregate on the basis of a time transition of the phase difference amount density.

2. The determination method according to claim 1, further comprising:
   a first process of differentiating stem cells into germ layers, the stem cells being the cells constituting the aggregate; and
   determining a state of differentiation of the aggregate to the germ layers on the basis of the time transition of the phase difference amount density after executing the first process.

3. The determination method according to claim 2, further comprising:
   determining a ratio of the cells differentiated into the germ layers among the stem cells on the basis of a degree of change in the phase difference amount density after executing the first process from the phase difference amount density before executing the first process.

4. The determination method according to claim 3, further comprising:
   a second process of further differentiating the cells, which has been differentiated into the germ layers, into specific cells after executing the first process; and
   determining a state of differentiation into the specific cells on the basis of the time transition of the phase difference amount density after executing the second process.

5. The determination method according to claim 4, further comprising:
   determining a ratio of the cells differentiated into the specific cells on the basis of a degree of change in the phase difference amount density after executing the second process from the phase difference amount density before executing the second process.

6. The determination method according to claim 2, further comprising:
   a second process of further differentiating the cells, which has been differentiated into the germ layers, into specific cells after executing the first process; and
   determining a state of differentiation into the specific cells on the basis of the time transition of the phase difference amount density after executing the second process.

7. The determination method according to claim 6, further comprising:
   determining a ratio of the cells differentiated into the specific cells on the basis of a degree of change in the phase difference amount density after executing the second process from the phase difference amount density before executing the second process.

8. The determination method according to claim 1, further comprising:
   a first process of differentiating stem cells into germ layers, the stem cells being the cells constituting the aggregate;
   a second process of further differentiating the cells, which has been differentiated into the germ layers, into specific cells after executing the first process; and
   performing a determination for a lot to be determined including a plurality of the aggregates on the basis of the time transition of the phase difference amount density from the execution of the first process to a lapse of a predetermined period after executing the second process.

9. The determination method according to claim 8, further comprising:
   performing a determination for the lot to be determined, on the basis of a degree of deviation from reference data of the time transition of the phase difference amount density, from the execution of the first process to the lapse of the predetermined period after executing of the second process, acquired for the lot to be determined.

10. The determination method according to claim 9, further comprising:
    deriving a correction value for each of the phase difference amount densities of a plurality of the aggregates included in the lot to be determined so as to suppress a dependency of the phase difference amount density of a plurality of the aggregates included in the lot to be determined on a particle diameter of the aggregate; and
    performing a determination for the lot to be determined on the basis of a time transition of the correction value.

11. The determination method according to claim 10, further comprising:
- deriving a value, as a correction coefficient, obtained by dividing a frequency in each class of a frequency distribution of particle diameters of a plurality of the aggregates included in an evaluation standard lot by a frequency in a corresponding class of a frequency distribution of the particle diameters of a plurality of the aggregates included in the lot to be determined;
- deriving a correction value of the phase difference amount density of a plurality of the aggregates included in the lot to be determined by multiplying the phase difference amount density acquired for each of a plurality of the aggregates included in the lot to be determined by a corresponding correction coefficient; and
- performing a determination for the lot to be determined on the basis of a time transition of an average value of the correction values.

12. The determination method according to claim 9, further comprising:
- deriving a value, as a correction coefficient, obtained by dividing a frequency in each class of a frequency distribution of particle diameters of a plurality of the aggregates included in an evaluation standard lot by a frequency in a corresponding class of a frequency distribution of the particle diameters of a plurality of the aggregates included in the lot to be determined;
- deriving a correction value of the phase difference amount density of a plurality of the aggregates included in the lot to be determined by multiplying the phase difference amount density acquired for each of a plurality of the aggregates included in the lot to be determined by a corresponding correction coefficient; and
- performing a determination for the lot to be determined on the basis of a time transition of an average value of the correction values.

13. The determination method according to claim 9, further comprising:
- deriving an index value indicating a correlation between the phase difference amount density and a particle diameter of the aggregate for a plurality of the aggregates included in the lot to be determined; and
- performing a determination for the lot to be determined on the basis of a time transition of the index value.

14. The determination method according to claim 8, further comprising:
- deriving a correction value for each of the phase difference amount densities of a plurality of the aggregates included in the lot to be determined so as to suppress a dependency of the phase difference amount density of a plurality of the aggregates included in the lot to be determined on a particle diameter of the aggregate; and
- performing a determination for the lot to be determined on the basis of a time transition of the correction value.

15. The determination method according to claim 10, further comprising:
- deriving a value, as a correction coefficient, obtained by dividing a frequency in each class of a frequency distribution of particle diameters of a plurality of the aggregates included in an evaluation standard lot by a frequency in a corresponding class of a frequency distribution of the particle diameters of a plurality of the aggregates included in the lot to be determined;
- deriving a correction value of the phase difference amount density of a plurality of the aggregates included in the lot to be determined by multiplying the phase difference amount density acquired for each of a plurality of the aggregates included in the lot to be determined by a corresponding correction coefficient; and
- performing a determination for the lot to be determined on the basis of a time transition of an average value of the correction values.

16. The determination method according to claim 8, further comprising:
- deriving a value, as a correction coefficient, obtained by dividing a frequency in each class of a frequency distribution of particle diameters of a plurality of the aggregates included in an evaluation standard lot by a frequency in a corresponding class of a frequency distribution of the particle diameters of a plurality of the aggregates included in the lot to be determined;
- deriving a correction value of the phase difference amount density of a plurality of the aggregates included in the lot to be determined by multiplying the phase difference amount density acquired for each of a plurality of the aggregates included in the lot to be determined by a corresponding correction coefficient; and
- performing a determination for the lot to be determined on the basis of a time transition of an average value of the correction values.

17. The determination method according to claim 8, further comprising:
- deriving an index value indicating a correlation between the phase difference amount density and a particle diameter of the aggregate for a plurality of the aggregates included in the lot to be determined; and
- performing a determination for the lot to be determined on the basis of a time transition of the index value.

* * * * *